US011274349B2

(12) United States Patent
Di Vizio et al.

(10) Patent No.: US 11,274,349 B2
(45) Date of Patent: Mar. 15, 2022

(54) METHODS FOR DIAGNOSING CANCER

(71) Applicant: Cedars-Sinai Medical Center, Los Angeles, CA (US)

(72) Inventors: Dolores Di Vizio, Los Angeles, CA (US); Valentina R. Minciacchi, Los Angeles, CA (US); Andrew Conley, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 55 days.

(21) Appl. No.: 16/335,605

(22) PCT Filed: Nov. 8, 2017

(86) PCT No.: PCT/US2017/060707
§ 371 (c)(1),
(2) Date: Mar. 21, 2019

(87) PCT Pub. No.: WO2018/089541
PCT Pub. Date: May 17, 2018

(65) Prior Publication Data
US 2019/0300966 A1 Oct. 3, 2019

Related U.S. Application Data

(60) Provisional application No. 62/419,302, filed on Nov. 8, 2016.

(51) Int. Cl.
*C12Q 1/6886* (2018.01)
*C12Q 1/6851* (2018.01)
*C12Q 1/68* (2018.01)

(52) U.S. Cl.
CPC .............. *C12Q 1/6886* (2013.01); *C12Q 1/68* (2013.01); *C12Q 1/6851* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 6,258,540 B1 | 7/2001 | Lo et al. | |
| 6,355,623 B2 | 3/2002 | Seidman et al. | |
| 6,812,023 B1 | 11/2004 | Lamparski et al. | |
| 10,254,285 B2 | 4/2019 | Di Vizio et al. | |
| 2006/0019256 A1 | 1/2006 | Clarke et al. | |
| 2008/0199890 A1 | 8/2008 | Letai | |
| 2010/0184046 A1 | 7/2010 | Klas et al. | |
| 2010/0196426 A1 | 8/2010 | Skog et al. | |
| 2010/0304989 A1 | 12/2010 | Von Hoff et al. | |
| 2011/0200998 A1 | 8/2011 | Weichselbaum et al. | |
| 2014/0038901 A1* | 2/2014 | Lyden ................ | C12Q 1/6886 514/19.8 |
| 2014/0045915 A1* | 2/2014 | Skog ................... | C12Q 1/6806 514/44 A |
| 2014/0056807 A1 | 2/2014 | Di Vizio et al. | |
| 2014/0148350 A1 | 5/2014 | Spetzler et al. | |
| 2015/0301055 A1* | 10/2015 | Spetzler ........... | G01N 33/57484 506/9 |
| 2016/0061842 A1 | 3/2016 | Di Vizio et al. | |
| 2020/0408766 A1 | 12/2020 | Di Vizio et al. | |

FOREIGN PATENT DOCUMENTS

| | | |
|---|---|---|
| EP | 2986326 B1 | 9/2018 |
| WO | WO 2012/115885 A1 | 8/2012 |
| WO | WO 2014/172390 A2 | 10/2014 |
| WO | WO 2018089541 A1 | 5/2018 |

OTHER PUBLICATIONS

Haynes et al Electrophoresis. 1998. 19: 1862-1871 (Year: 1998).*
Chen et al Molecular & Cellular Proteomics. 2002. 1: 304-313 (Year: 2002).*
Vogel et al Nature Review Genet. Mar. 2012. 13(4): 227-232 (Year: 2012).*
Conley et al. J Extracell Vesicles. Apr. 21, 2015. 4:10, abstract O-7C-6 (Year: 2015).*
Spinelli et al. J Extracell Vesicles. Apr. 21, 2015. 4:10, abstract O-5A-6 (Year: 2015).*
Conley et al. Feb. 21, 2017 Supplementary Tables, available via URL: <.tandfonline.com/doi/full/10.1080/15476286.2016.1259061#supplemental-material-section>, p. 1-890 (from RNA Biology, 14(3): 305-316. 2017) (Year: 2017).*
International Search Report and Written Opinion of PCT/US2017/60707, dated Mar. 29, 2018, 11 Pages.
International Preliminary Report on Patentability of PCT/US2014/034245 dated Oct. 20, 2015; 8 pages.
International Search Report and Written Opinion of PCT/US2014/034245 dated Nov. 7, 2014; 13 pages.
Extended Search Report of EP Application No. 14785880.7 dated Dec. 19, 2016; 13 pages.
Adlard et al.. Prediction of the Response of Colorectal Cancer to Systemic Therapy, The Lancet Oncology, 2002, vol. 3, pp. 75-82.
Bhardwaj et al. Physicochemical properties of extruded and non-extruded liposomes containing the hydrophobic drug dexamethasone. International Journal of Pharmaceutics (2010). 388:181-189.
Chambers et al. Microvesicle-mediated release of soluble LH/hCG receptor (LHCGR) from transfected cells and placenta explants. Reproductive Biology and Endocrinology (2011). 9:64 (15 pages).
Cheruvanky et al. Rapid isolation of urinary exosomal biomarkers using a nanomembrane ultrafiltration concentrator. Am J Physiol Renal Physiol (2007). 292:F1657-F1661.
Conley et al., High-Throughput Sequencing of Two Populations of Extracellular Vesicles as mRNA Signature that can be Detected in the Circulation of Breast Cancer Patients, 2017, RNA Biology, vol. 14(3), pp. 305-316.

(Continued)

*Primary Examiner* — Carla J Myers
(74) *Attorney, Agent, or Firm* — Linda B. Huber; Nixon Peabody LLP

(57) ABSTRACT

Provided herein are methods for diagnosing cancer in a subject by determining the gene expression level of one or more genes in extracellular vesicles isolated from samples obtained from a subject.

7 Claims, 8 Drawing Sheets

Specification includes a Sequence Listing.

(56) References Cited

OTHER PUBLICATIONS

D'Asti et al. Oncogenic extracellular vesicles in brain tumor progression. Frontiers in Physiology (2012). 3:Article 294 (15 pages).
Di Vizio et al. Large Oncosomes in Human Prostate Cancer Tissues and in the Circulation of Mice with Metastatic Disease. The American Journal of Pathology (2012). 181(5):1573-1584.
Di Vizio et al. Oncosome Formation in Prostate Cancer: Association with a Region of Frequent Chromosomal Deletion in Metastatic Disease. Cancer Research (2009). 69:5601-5609.
Dragovic et al. Sizing and phenotyping of cellular vesicles using Nanoparticle Tracking Analysis. Nanomedicine: Nanotechnology, Biology, and Medicine (2011). 7:780-788.
D'Souza-Schorey et al. Tumor-derived microvesicles: shedding light on novel microenvironment modulators and prospective cancer biomarkers. Genes & Development (2012). 1287-1299.
Fiskaa et al., Distinct Small RNA Signatures in Extracellular Vesicles Derived from Breast Cancer Cell Lines, 2016, PLoS One, vol. 11(8), e0161824, 18 Pages.
Floryan et al. Intraoperative use of autologous platelet-rich and platelet-poor plasma for orthopedic surgery patients. AORN Journal (2004). 80:668-674.
Freshney, Culture of Animal Cells, A Manual of Basic Technique, 1983, pp. 1-4.
Fujita et al., Extracellular Vesicle Transfer of Cancer Pathogenic Components, 2016, Cancer Science, vol. 107(4), pp. 385-390.
Gerdes et al., Emerging Understanding of Multiscale Tumor Heterogeneity, Frontiers in Oncology, 2014, 4(Article 366), pp. 1-12.
Kaiser, First Pass at Cancer Genome Reveals Complex Landscape, Science, 2006, vol. 313, p. 1370.
Morello et al. Abstract 430: MiRNA profiling of prostate cancer cell-derived large oncosomes identifies a signature of invasion and metastasis. Cancer Research (2012). 72(5): Suppl 1 (1 page).
Morello et al. Large oncosomes mediate intercellular transfer of functional microRNA. Cell Cycle (2013). 12(22):3526-3536.
Muralidharan-Chari et al. Microvesicles: mediators of extracellular communication during cancer progression. Journal of Cell Science (2010). 123:1603-1611.
Myers et al. Successful Treatment of Advanced Metastatic Prostate Cancer following Chemotherapy Based on Molecular Profiling. Case Reports in Oncology (2012). 5(1):154-158.
Peinado et al. Melanoma exosomes educate bone marrow progenitor cells toward a pro-metastatic phenotype through MET. Nat Med (2012). 18(6):883-891.
Pritzker. K., Cancer Biomarkers: Easier Said Than Done, Clinical Chemistry, 2002, vol. 48(8), pp. 1147-1150.
Response to Office Action (dated Jul. 9, 2018) of U.S. Appl. No. 14/883,421, filed Sep. 28, 2018, 5 Pages.
Response to Office Action (dated Jun. 28, 2018) of U.S. Appl. No. 13/975,059, filed Sep. 28, 2018, 11 Pages.
Shao et al. Protein typing of circulating microvesicles allows real-time monitoring of gliobastoma therapy. Nat Med (2012). 18(12):1835-1840.
Skog et al., Glioblastoma Microvesicles Transport RNA and Proteins that Promote Tumour Growth and Provide Diagnostic Biomarkers, 2008, Nat. Cell. Bio., vol. 10(12), pp. 1470-1476.
Tian et al., The Expression of Native and Cultured RPE Grown on Different Matrices, Physiol Genomics, 2004, vol. 17, pp. 170-182.
Xiao et al. Effect of 5-Aza-2' deoxycytidine on immune-associated proteins in exosomes from hepatoma. World Journal of Gastroenterology (2010). 16(19):2371-2377.
Zips et al., New Anticancer Agents: In Vitro and In Vivo Evaluation, In Vivo, 2005, vol. 19, pp. 1-8.

\* cited by examiner

Cellular Component

Molecular Function

Biological Pathway

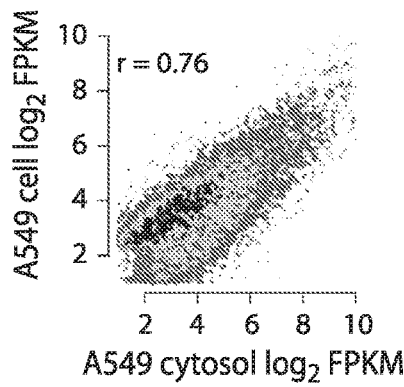
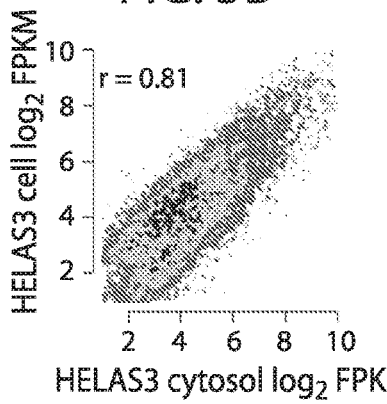
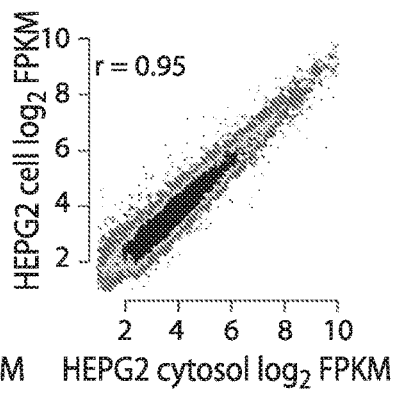
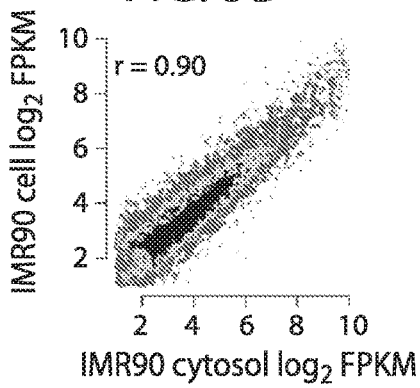
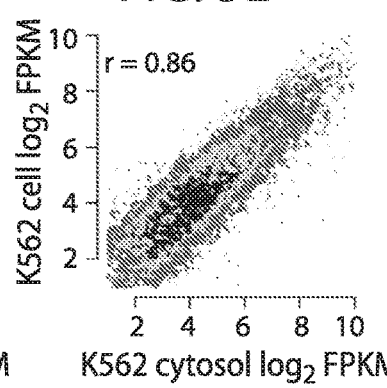
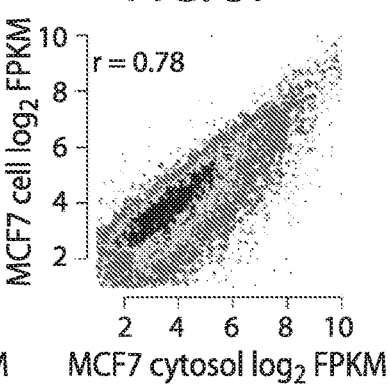
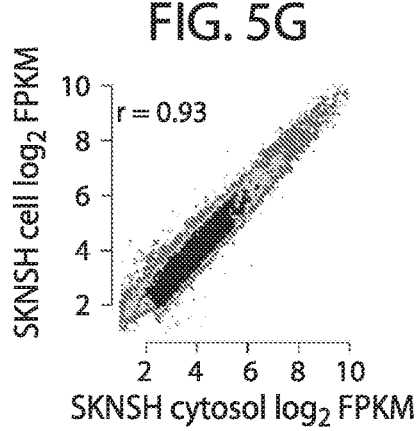

SEQUENCE LISTING

```
<160> NUMBER OF SEQ ID NOS: 50

<210> SEQ ID NO 1
<211> LENGTH: 19
<212> TYPE: DNA
<213> ORGANISM: Artificial Sequence
<220> FEATURE:
<223> OTHER INFORMATION: Synthetic

<400> SEQUENCE: 1
cttgccttgc tgctctacc                                                    19

<210> SEQ ID NO 2
<211> LENGTH: 19
<212> TYPE: DNA
<213> ORGANISM: Artificial Sequence
<220> FEATURE:
<223> OTHER INFORMATION: Synthetic

<400> SEQUENCE: 2
cacacaggat ggcttgaag                                                    19

<210> SEQ ID NO 3
<211> LENGTH: 21
<212> TYPE: DNA
<213> ORGANISM: Artificial Sequence
<220> FEATURE:
<223> OTHER INFORMATION: Synthetic

<400> SEQUENCE: 3
```
acaatgaggc tggcaagatc a                    21

<210> SEQ ID NO 4
<211> LENGTH: 20
<212> TYPE: DNA
<213> ORGANISM: Artificial Sequence
<220> FEATURE:
<223> OTHER INFORMATION: Synthetic

<400> SEQUENCE: 4
acccactcgc tggcttttaa                      20

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
tgcagaagta cctggaggac                      20

<210> SEQ ID NO 6
<211> LENGTH: 21
<212> TYPE: DNA
<213> ORGANISM: Artificial Sequence
<220> FEATURE:
<223> OTHER INFORMATION: Synthetic

<400> SEQUENCE: 6
gaagtctcgg aagagcaggt a                    21

<210> SEQ ID NO 7
<211> LENGTH: 19
<212> TYPE: DNA
<213> ORGANISM: Artificial Sequence
<220> FEATURE:
<223> OTHER INFORMATION: Synthetic

<400> SEQUENCE: 7
gggccattgc aggcaatcc                       19

<210> SEQ ID NO 8
<211> LENGTH: 22
<212> TYPE: DNA
<213> ORGANISM: Artificial Sequence
<220> FEATURE:
<223> OTHER INFORMATION: Synthetic

<400> SEQUENCE: 8
tgttgagagt gatggcccca aa                   22

<210> SEQ ID NO 9
<211> LENGTH: 21
<212> TYPE: DNA
<213> ORGANISM: Artificial Sequence
<220> FEATURE:
<223> OTHER INFORMATION: Synthetic

<400> SEQUENCE: 9
gatctatgac gccgagaagc a                    21

<210> SEQ ID NO 10
<211> LENGTH: 22
<212> TYPE: DNA
<213> ORGANISM: Artificial Sequence
<220> FEATURE:
<223> OTHER INFORMATION: Synthetic

<400> SEQUENCE: 10
ccactgattg ttcgtcctcg aa        22

<210> SEQ ID NO 11
<211> LENGTH: 22
<212> TYPE: DNA
<213> ORGANISM: Artificial Sequence
<220> FEATURE:
<223> OTHER INFORMATION: Synthetic

<400> SEQUENCE: 11
agctcattgc caagaagtcc aa        22

<210> SEQ ID NO 12
<211> LENGTH: 19
<212> TYPE: DNA
<213> ORGANISM: Artificial Sequence
<220> FEATURE:
<223> OTHER INFORMATION: Synthetic

<400> SEQUENCE: 12
tcctgggtca acccctcaa        19

<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13
tctcctgccg acaagaccaa        20

<210> SEQ ID NO 14
<211> LENGTH: 19
<212> TYPE: DNA
<213> ORGANISM: Artificial Sequence
<220> FEATURE:
<223> OTHER INFORMATION: Synthetic

<400> SEQUENCE: 14
gtggtgggga aggacagga        19

<210> SEQ ID NO 15
<211> LENGTH: 18
<212> TYPE: DNA
<213> ORGANISM: Artificial Sequence
<220> FEATURE:
<223> OTHER INFORMATION: Synthetic

<400> SEQUENCE: 15
ccactgcctg ctggtgac        18

<210> SEQ ID NO 16
<211> LENGTH: 20
<212> TYPE: DNA
<213> ORGANISM: Artificial Sequence
<220> FEATURE:
<223> OTHER INFORMATION: Synthetic

<400> SEQUENCE: 16
taccgaggct ccagcttaac        20

```
<210> SEQ ID NO 17
<211> LENGTH: 20
<212> TYPE: DNA
<213> ORGANISM: Artificial Sequence
<220> FEATURE:
<223> OTHER INFORMATION: Synthetic

<400> SEQUENCE: 17
cgctgaggct tatttgggaa                                              20

<210> SEQ ID NO 18
<211> LENGTH: 20
<212> TYPE: DNA
<213> ORGANISM: Artificial Sequence
<220> FEATURE:
<223> OTHER INFORMATION: Synthetic

<400> SEQUENCE: 18
ttggcgttgg gcatcattaa                                              20

<210> SEQ ID NO 19
<211> LENGTH: 19
<212> TYPE: DNA
<213> ORGANISM: Artificial Sequence
<220> FEATURE:
<223> OTHER INFORMATION: Synthetic

<400> SEQUENCE: 19
atcctgccgt ccttctcca                                               19

<210> SEQ ID NO 20
<211> LENGTH: 20
<212> TYPE: DNA
<213> ORGANISM: Artificial Sequence
<220> FEATURE:
<223> OTHER INFORMATION: Synthetic

<400> SEQUENCE: 20
ccatggacag gatgaagtcc                                              20

<210> SEQ ID NO 21
<211> LENGTH: 21
<212> TYPE: DNA
<213> ORGANISM: Artificial Sequence
<220> FEATURE:
<223> OTHER INFORMATION: Synthetic

<400> SEQUENCE: 21
gtaacaggca aagctgatgc a                                            21

<210> SEQ ID NO 22
<211> LENGTH: 20
<212> TYPE: DNA
<213> ORGANISM: Artificial Sequence
<220> FEATURE:
<223> OTHER INFORMATION: Synthetic

<400> SEQUENCE: 22
agccccaaac ttgtctggaa                                              20

<210> SEQ ID NO 23
<211> LENGTH: 21
<212> TYPE: DNA
<213> ORGANISM: Artificial Sequence
<220> FEATURE:
<223> OTHER INFORMATION: Synthetic
```

-continued

<400> SEQUENCE: 23
acccattcca ccttactacc a                                              21

<210> SEQ ID NO 24
<211> LENGTH: 20
<212> TYPE: DNA
<213> ORGANISM: Artificial Sequence
<220> FEATURE:
<223> OTHER INFORMATION: Synthetic

<400> SEQUENCE: 24
tctattgcgc cggtttacaa                                                20

<210> SEQ ID NO 25
<211> LENGTH: 20
<212> TYPE: DNA
<213> ORGANISM: Artificial Sequence
<220> FEATURE:
<223> OTHER INFORMATION: Synthetic

<400> SEQUENCE: 25
ctaaccgtgc aaaggtagca                                                20

<210> SEQ ID NO 26
<211> LENGTH: 20
<212> TYPE: DNA
<213> ORGANISM: Artificial Sequence
<220> FEATURE:
<223> OTHER INFORMATION: Synthetic

<400> SEQUENCE: 26
ggtcagttgc agtggttgaa                                                20

<210> SEQ ID NO 27
<211> LENGTH: 21
<212> TYPE: DNA
<213> ORGANISM: Artificial Sequence
<220> FEATURE:
<223> OTHER INFORMATION: Synthetic

<400> SEQUENCE: 27
caacagtgac gtgttctcca a                                              21

<210> SEQ ID NO 28
<211> LENGTH: 20
<212> TYPE: DNA
<213> ORGANISM: Artificial Sequence
<220> FEATURE:
<223> OTHER INFORMATION: Synthetic

<400> SEQUENCE: 28
caaagttgtt ccggccttca                                                20

<210> SEQ ID NO 29
<211> LENGTH: 20
<212> TYPE: DNA
<213> ORGANISM: Artificial Sequence
<220> FEATURE:
<223> OTHER INFORMATION: Synthetic

<400> SEQUENCE: 29
ttctgctccg tgtgtaacca                                                20

<210> SEQ ID NO 30

```
<211> LENGTH: 22
<212> TYPE: DNA
<213> ORGANISM: Artificial Sequence
<220> FEATURE:
<223> OTHER INFORMATION: Synthetic

<400> SEQUENCE: 30
attatagagg gccaggtgaa cc                                          22

<210> SEQ ID NO 31
<211> LENGTH: 21
<212> TYPE: DNA
<213> ORGANISM: Artificial Sequence
<220> FEATURE:
<223> OTHER INFORMATION: Synthetic

<400> SEQUENCE: 31
tcagcaagtg gaccttttga a                                           21

<210> SEQ ID NO 32
<211> LENGTH: 21
<212> TYPE: DNA
<213> ORGANISM: Artificial Sequence
<220> FEATURE:
<223> OTHER INFORMATION: Synthetic

<400> SEQUENCE: 32 caagggatg actaggcaaa a                                            21

<210> SEQ ID NO 33
<211> LENGTH: 21
<212> TYPE: DNA
<213> ORGANISM: Artificial Sequence
<220> FEATURE:
<223> OTHER INFORMATION: Synthetic

<400> SEQUENCE: 33
atcctggctg ctcttgagaa a                                           21

<210> SEQ ID NO 34
<211> LENGTH: 20
<212> TYPE: DNA
<213> ORGANISM: Artificial Sequence
<220> FEATURE:
<223> OTHER INFORMATION: Synthetic

<400> SEQUENCE: 34
gctcgtactc tgccacaaac                                             20

<210> SEQ ID NO 35
<211> LENGTH: 19
<212> TYPE: DNA
<213> ORGANISM: Artificial Sequence
<220> FEATURE:
<223> OTHER INFORMATION: Synthetic

<400> SEQUENCE: 35
agaagctgct gtcgcctaa                                              19

<210> SEQ ID NO 36
<211> LENGTH: 20
<212> TYPE: DNA
<213> ORGANISM: Artificial Sequence
<220> FEATURE:
<223> OTHER INFORMATION: Synthetic

<400> SEQUENCE: 36
```
cttgagcaca gagcaatgca                                              20

<210> SEQ ID NO 37
<211> LENGTH: 18
<212> TYPE: DNA
<213> ORGANISM: Artificial Sequence
<220> FEATURE:
<223> OTHER INFORMATION: Synthetic

<400> SEQUENCE: 37
gcagcaagcg atggcata                                                18

<210> SEQ ID NO 38
<211> LENGTH: 20
<212> TYPE: DNA
<213> ORGANISM: Artificial Sequence
<220> FEATURE:
<223> OTHER INFORMATION: Synthetic

<400> SEQUENCE: 38
gaaacagcgg gcttctgtaa                                              20

<210> SEQ ID NO 39
<211> LENGTH: 19
<212> TYPE: DNA
<213> ORGANISM: Artificial Sequence
<220> FEATURE:
<223> OTHER INFORMATION: Synthetic

<400> SEQUENCE: 39
ttcggggtct ggtggaaaa                                               19

<210> SEQ ID NO 40
<211> LENGTH: 20
<212> TYPE: DNA
<213> ORGANISM: Artificial Sequence
<220> FEATURE:
<223> OTHER INFORMATION: Synthetic

<400> SEQUENCE: 40
cctgcatgag cttctgacac                                              20

<210> SEQ ID NO 41
<211> LENGTH: 19
<212> TYPE: DNA
<213> ORGANISM: Artificial Sequence
<220> FEATURE:
<223> OTHER INFORMATION: Synthetic

<400> SEQUENCE: 41
gggccgatgt tctcaggaa                                               19

<210> SEQ ID NO 42
<211> LENGTH: 22
<212> TYPE: DNA
<213> ORGANISM: Artificial Sequence
<220> FEATURE:
<223> OTHER INFORMATION: Synthetic

<400> SEQUENCE: 42
cttgatcacc aggcacttgt ac                                           22

<210> SEQ ID NO 43
<211> LENGTH: 21
<212> TYPE: DNA

<213> ORGANISM: Artificial Sequence
<220> FEATURE:
<223> OTHER INFORMATION: Synthetic

<400> SEQUENCE: 43
gatcagcaag aatgtcactc c                                              21

<210> SEQ ID NO 44
<211> LENGTH: 23
<212> TYPE: DNA
<213> ORGANISM: Artificial Sequence
<220> FEATURE:
<223> OTHER INFORMATION: Synthetic

<400> SEQUENCE: 44
tctctgggaa ccttcatatt cac                                            23

<210> SEQ ID NO 45
<211> LENGTH: 21
<212> TYPE: DNA
<213> ORGANISM: Artificial Sequence
<220> FEATURE:
<223> OTHER INFORMATION: Synthetic

<400> SEQUENCE: 45
ggtcctttcc gacaagctga a                                              21

<210> SEQ ID NO 46
<211> LENGTH: 22
<212> TYPE: DNA
<213> ORGANISM: Artificial Sequence
<220> FEATURE:
<223> OTHER INFORMATION: Synthetic

<400> SEQUENCE: 46
agttactgac ctctccgcaa ac                                             22

<210> SEQ ID NO 47
<211> LENGTH: 18
<212> TYPE: DNA
<213> ORGANISM: Artificial Sequence
<220> FEATURE:
<223> OTHER INFORMATION: Synthetic

<400> SEQUENCE: 47
tcaaggactt ggcctcca                                                  18

<210> SEQ ID NO 48
<211> LENGTH: 20
<212> TYPE: DNA
<213> ORGANISM: Artificial Sequence
<220> FEATURE:
<223> OTHER INFORMATION: Synthetic

<400> SEQUENCE: 48
cctcaaggct ggcttcaata                                                20

<210> SEQ ID NO 49
<211> LENGTH: 17
<212> TYPE: DNA
<213> ORGANISM: Artificial Sequence
<220> FEATURE:
<223> OTHER INFORMATION: Synthetic

<400> SEQUENCE: 49
gcggcttggc ggagatt                                                   17

```
<210> SEQ ID NO 50
<211> LENGTH: 20
<212> TYPE: DNA
<213> ORGANISM: Artificial Sequence
<220> FEATURE:
<223> OTHER INFORMATION: Synthetic

<400> SEQUENCE: 50
ttccacggcc tggtcttttg                                              20
```

US 11,274,349 B2

METHODS FOR DIAGNOSING CANCER

CROSS-REFERENCE TO RELATED APPLICATIONS

This application is a National Phase of International Application No. PCT/US2017/060707 filed Nov. 8, 2017, currently pending, which designated the U.S. and that International Application was published under PCT Article 21(2) in English, which also includes a claim of priority under 35 U.S.C. § 119(e) to U.S. provisional patent application No. 62/419,302 filed Nov. 8, 2016, the entirety of which is hereby incorporated by reference.

STATEMENT REGARDING FEDERALLY SPONSORED RESEARCH OR DEVELOPMENT

This invention was made with government support under Grant No. CA131472 awarded by National Institutes of Health. The government has certain rights in the invention.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Early detection of cancer allows for rapid and effective treatment of the cancer. There is a need in the art for rapid tests, including blood tests, that allow for early detection of cancer.

Herein, the inventors provide methods for diagnosing cancer in subjects by detecting gene expression markers in extracellular vesicles isolated from a sample obtained from a subject.

SUMMARY OF THE INVENTION

The following embodiments and aspects thereof are described and illustrated in conjunction with systems, compositions and methods which are meant to be exemplary and illustrative, not limiting in scope.

Provided herein is a method comprising determining the likelihood of cancer in a subject in need thereof. The method comprises: obtaining results of expression levels of any one or more or all histone genes and any one or more or all of E2F target genes in extracellular vesicles isolated from a sample obtained from the subject; and determining that the subject has an increased likelihood of cancer if the extracellular vesicles isolated from the sample obtained from the subject comprise increased expression of the histone genes and E2F target genes relative to the reference value so as to determine the likelihood of cancer in the subject. In various embodiments, the histone genes are any one or more or all of HIST1H3F, HIST1H3G, HIST1H2AJ, HIST1H2BM, HIST1H1B, HIST1H3B, HIST1H2AH, HIST1H3J, HIST1H2BI, HIST1H2BO and HIST1H2AI genes. In various embodiments, the E2F target genes are any one or more or all of SPC24, CENPF, ARHGAP11B, CEP128, QPCTL, HMMR, HIST1H2BL, NDC80, KIF15, HMBS, ABCB6, HIST1H2BM, GUCY1B3, SYNGR4, RECQL4, CDCA7, TTK, CKAP2, BORA and CENPW. In some embodiments, the subject has or is suspected of having cancer or is desiring determination of likelihood of having cancer. In various embodiments, the extracellular vesicles are exosomes, large oncosomes, microvesicles or a combination thereof.

Also provided herein is a method comprising: determining the likelihood of cancer in a subject in need thereof and selecting or prescribing a therapy for cancer if increased likelihood of cancer is determined. The method for determining the likelihood of cancer in the subject comprises: obtaining results of expression of any one or more or all histone genes and any one or more or all of E2F target genes in extracellular vesicles isolated from a sample obtained from the subject; and determining that the subject has an increased likelihood of cancer if the extracellular vesicles isolated from the sample from the subject comprise increased expression of the histone genes and E2F target genes relative to the reference value so as to determine the likelihood of cancer in the subject. In various embodiments, the histone genes are any one or more or all of HIST1H3F, HIST1H3G, HIST1H2AJ, HIST1H2BM, HIST1H1B, HIST1H3B, HIST1H2AH, HIST1H3J, HIST1H2BI, HIST1H2BO and HIST1H2AI genes. In various embodiments, the E2F targets are any one or more or all of SPC24, CENPF, ARHGAP11B, CEP128, QPCTL, HMMR, HIST1H2BL, NDC80, KIF15, HMBS, ABCB6, HIST1H2BM, GUCY1B3, SYNGR4, RECQL4, CDCA7, TTK, CKAP2, BORA and CENPW. In some embodiments, the subject has or is suspected of having cancer or is desiring determination of likelihood of having cancer. In various embodiments, the extracellular vesicles are exosomes, large oncosomes, microvesicles or a combination thereof.

Also provided herein is a method for determining the likelihood of breast cancer in a subject in need thereof. The method comprises: obtaining results of expression of any one or more or all of NXF3, LOC650293, PAM16, PRB2, ANP32c, KRTAP10-12, APOBEC3H, SPC24, PRB4, LHB, S100A3 and SSX7 genes in extracellular vesicles isolated from a sample obtained from the subject; and determining that the subject has an increased likelihood of breast cancer if the extracellular vesicles isolated from the sample from the subject comprise increased expression of any one or more or all of the NXF3, LOC650293, PAM16, PRB2, ANP32c, KRTAP10-12, APOBEC3H, SPC24, PRB4, LHB, S100A3 and SSX7 genes relative to the reference value so as to determine the likelihood of breast cancer in the subject. In some embodiments, the subject has or is suspected of having cancer or is desiring determination of likelihood of having cancer. In various embodiments, the extracellular vesicles are exosomes, large oncosomes, microvesicles or a combination thereof.

Also provided herein is a method comprising: determining the likelihood of breast cancer in a subject in need thereof and selecting or prescribing a therapy for breast cancer if increased likelihood of breast cancer is determined. The method for determining the likelihood of breast cancer in the subject comprises: obtaining results of expression of any one or more or all of NXF3, LOC650293, PAM16, PRB2, ANP32c, KRTAP10-12, APOBEC3H, SPC24, PRB4, LHB, S100A3 and SSX7 genes in extracellular vesicles isolated from a sample obtained from the subject; and determining that the subject has an increased likelihood of breast cancer if the extracellular vesicles isolated from the sample from the subject comprise increased expression of any one or more of the NXF3, LOC650293, PAM16, PRB2, ANP32c, KRTAP10-12, APOBEC3H, SPC24, PRB4, LHB, S100A3 and SSX7 genes relative to the reference value so as to determine the likelihood of breast cancer in the subject.

In some embodiments, the subject has or is suspected of having cancer or is desiring determination of likelihood of having cancer. In various embodiments, the extracellular vesicles are exosomes, large oncosomes, microvesicles or a combination thereof.

Further provided herein is a method for determining the likelihood of glioblastoma in a subject in need thereof. The method comprises: obtaining results of expression of any one or more or all of UBC, HIST1H3F, HIST1H3G, HIST1H2AJ, HIST1H2BM, HIST1H1B, UBE2C, TK1, MYBL2, HIST1H3B, HIST1H2AH, RRM2, HIST1H3J, HIST1H2BI, HIST1H2BO, HIST1H2AI, ANLN, ARHGAP11A, RAB13, ZWINT genes in extracellular vesicles isolated from a sample obtained from the subject; and determining that the subject has an increased likelihood of glioblastoma if the extracellular vesicles isolated sample from the subject comprise increased expression of any one or more or all of the UBC, HIST1H3F, HIST1H3G, HIST1H2AJ, HIST1H2BM, HIST1H1B, UBE2C, TK1, MYBL2, HIST1H3B, HIST1H2AH, RRM2, HIST1H3J, HIST1H2BI, HIST1H2BO, HIST1H2AI, ANLN, ARHGAP11A, RAB13, ZWINT genes relative to the reference value so as to determine the likelihood of glioblastoma in the subject. In some embodiments, the subject has or is suspected of having cancer or is desiring determination of likelihood of having cancer. In various embodiments, the extracellular vesicles are exosomes, large oncosomes, microvesicles or a combination thereof.

Also provided herein is a method comprising: determining the likelihood of glioblastoma in a subject in need thereof and selecting or prescribing a therapy for glioblastoma if increased likelihood of glioblastoma is determined. The method for determining the likelihood of glioblastoma in the comprises: obtaining results of expression of any one or more or all of UBC, HIST1H3F, HIST1H3G, HIST1H2AJ, HIST1H2BM, HIST1H1B, UBE2C, TK1, MYBL2, HIST1H3B, HIST1H2AH, RRM2, HIST1H3J, HIST1H2BI, HIST1H2BO, HIST1H2AI, ANLN, ARHGAP11A, RAB13, ZWINT genes in extracellular vesicles isolated from a sample obtained from the subject; and determining that the subject has an increased likelihood of glioblastoma if the extracellular vesicles isolated from sample obtained from the subject comprise increased expression of any one or more or all of the UBC, HIST1H3F, HIST1H3G, HIST1H2AJ, HIST1H2BM, HIST1H1B, UBE2C, TK1, MYBL2, HIST1H3B, HIST1H2AH, RRM2, HIST1H3J, HIST1H2BI, HIST1H2BO, HIST1H2AI, ANLN, ARHGAP11A, RAB13, ZWINT genes relative to the reference value so as to determine the likelihood of glioblastoma in the subject. In some embodiments, the subject has or is suspected of having cancer or is desiring determination of likelihood of having cancer. In various embodiments, the extracellular vesicles are exosomes, large oncosomes, microvesicles or a combination thereof.

Also provided herein is a method for determining the likelihood of invasive lobular carcinoma (ILC) in a subject in need thereof. The method comprises obtaining results of expression of any one or more or all of KRTAP6-1, HBG1, AHSP, SPC24, HBE1, KCNH2, SLC43A1, CENPF, KRTAP13-3, MT1A, FHDC1, SMR3A, SPTA1, CA1, TSPO2 genes in extracellular vesicles isolated from a sample obtained from a subject; and determining that the subject has an increased likelihood of invasive lobular carcinoma if the extracellular vesicles isolated from the sample from the subject comprise increased expression of any one or more or all of the KRTAP6-1, HBG1, AHSP, SPC24, HBE1, KCNH2, SLC43A1, CENPF, KRTAP13-3, MT1A, FHDC1, SMR3A, SPTA1, CA1, TSPO2 genes relative to the reference value so as to determine the likelihood of invasive lobular carcinoma in the subject. In some embodiments, the subject has or is suspected of having cancer or is desiring determination of likelihood of having cancer. In various embodiments, the extracellular vesicles are exosomes, large oncosomes, microvesicles or a combination thereof.

Also provided herein is a method comprising: determining the likelihood of invasive lobular carcinoma in a subject in need thereof and selecting or prescribing a therapy for invasive lobular carcinoma if increased likelihood of invasive lobular carcinoma is determined. The method for determining the likelihood of invasive lobular carcinoma (ILC) in the subject comprises obtaining results of expression of any one or more or all of KRTAP6-1, HBG1, AHSP, SPC24, HBE1, KCNH2, SLC43A1, CENPF, KRTAP13-3, MT1A, FHDC1, SMR3A, SPTA1, CA1, TSPO2 genes in extracellular vesicles isolated from a sample obtained from a subject; and determining that the subject has an increased likelihood of invasive lobular carcinoma if the extracellular vesicles isolated from the sample from the subject comprise increased expression of any one or more or all of the KRTAP6-1, HBG1, AHSP, SPC24, HBE1, KCNH2, SLC43A1, CENPF, KRTAP13-3, MT1A, FHDC1, SMR3A, SPTA1, CA1, TSPO2 genes relative to the reference value so as to determine the likelihood of invasive lobular carcinoma in the subject. In some embodiments, the subject has or is suspected of having cancer or is desiring determination of likelihood of having cancer. In various embodiments, the extracellular vesicles are exosomes, large oncosomes, microvesicles or a combination thereof.

In various embodiments of the methods described herein, the expression level of the genes described herein is determined by detecting the level of mRNA encoded by the gene.

In various embodiments of the methods described herein, the extracellular vesicles are exosomes, large oncosomes, microvesicles or a combination thereof.

In exemplary embodiments of the methods described herein, the sample is blood, plasma or combination thereof.

In exemplary embodiments of the methods described herein, the sample is obtained from the subject before, during or after treatment for cancer.

In various embodiments of the methods described herein, the subject is human.

In some embodiments of the methods described herein, the reference value is the mean or median levels of expression of the genes described herein in a population of subjects that do not have cancer. In some embodiments of the methods described herein, the reference value is the mean or median levels of expression of the genes described herein in a population of subjects that have cancer in remission. In some embodiments of the methods described herein, the reference value is the mean or median levels of expression of the genes described herein in the subject from a different (for example, an earlier) time point.

In some embodiments of the methods described herein, the reference value is the mean or median levels of the mRNA encoded by the genes described herein, in a population of subjects that do not have cancer. In some embodiments of the methods described herein, the reference value is the mean or median levels of the mRNA encoded by the genes described herein, in a population of subjects that have cancer in remission. In some embodiments of the methods described herein, reference value is the mean or median levels of the mRNA encoded by the genes described herein, obtained from the subject at a difference time point.

Further provided herein is a method for treating cancer in a subject in need thereof comprising, diagnosing the likelihood of cancer by the methods described herein and administering an effective amount of one or more therapeutic agents described herein to the subject diagnosed with cancer.

Also provided herein is a method for treating breast cancer in a subject in need thereof comprising, diagnosing the likelihood of breast cancer by the methods described herein and administering an effective amount of one or more therapeutic agents described herein to the subject diagnosed with breast cancer.

Further provided herein is a method for treating glioblastoma in a subject in need thereof comprising, diagnosing the likelihood of glioblastoma by the method described herein and administering an effective amount of one or more therapeutic agents described herein to the subject diagnosed with glioblastoma.

Also provided herein is a method for treating invasive lobular carcinoma in a subject in need thereof comprising, diagnosing the likelihood of invasive lobular carcinoma by the methods described herein and administering an effective amount of one or more therapeutic agents described herein to the subject diagnosed with invasive lobular carcinoma.

BRIEF DESCRIPTION OF THE DRAWINGS

Exemplary embodiments are illustrated in references figures. It is intended that the embodiments and figures disclosed herein are to be considered illustrative rather than restrictive.

FIG. 1A: the purity of LO and Exo fractions was confirmed via Western blotting for HSPA5, GAPDH, and CD81. FIG. 1B: the electropherograms show the time distribution and fluorescence intensity (FU) of total RNA in LO, Exo, and cells. FIG. 1C: RNA yields from U87 LO were substantially higher than RNA yields from U87 Exo. FIG. 1D: the mRNA profiles of the Exo and LO EV fractions correlate very well (r=0.94). FIG. 1E-FIG. 1F: The mRNA profiles of both Exo and LO exhibited significant differences with the mRNA profile of U87 donor cells (r=0.74, and 0.73 respectively). FIG. 1G: The mRNA in U87 LO is less unspliced (more spliced) than the mRNA in U87 cells. The fraction of unspliced RNA-Seq reads was calculated for each gene in U87 LO and U87 cell data sets, in comparison with ENCODE RNA-Seq database on whole cell, cytosol, and nucleus from various cancer cell lines. *–p<0.001. FIG. 1H: U87 LO and Exo fractions are enriched for short mRNA transcripts in comparison with U87 cells. The annotated transcript length was found for mRNAs enriched or depleted in U87 EVs versus cells, and in ENCODE cytosol versus whole-cells.

FIG. 2A: U87 EVs are depleted for mRNAs encoding a signal peptide, and enriched for E2F4 targets and histone mRNAs. The only phase of the cell cycle in which both E2F targets and histone mRNAs are upregulated simultaneously is the S-phase, which suggests that mRNA export in LO occurs in S-phase. The fold-changes of genes in the three gene sets were found between U87 EVs and cells. Density is displayed as the estimated density of genes in each gene set in 1024 ranked bins. FIG. 2B: Expression microarray data comparing mRNA in EVs and cells from the indicated cell lines recapitulate the signal peptide (cyan) and the E2F4 target (light purple) patterns observed in the U87 EVs and cells. A depletion of signal peptide bearing mRNAs and an enrichment of E2F4 targets were observed in EVs from U87, SW480, and MDA-MB-231. *–p<0.001. FIG. 2C: U87 cells stably expressing DHB-YFP (green) were used for immunofluorescence imaging. Non-apoptotic blebbing, which results in LO formation, is associated with translocation of DHB-YPF from the nucleus to the cytoplasm, indicating that the cells are in the S-phase of the cell cycle when LO formation occurs. A representative confocal image is shown. Nuclei were stained with DAPI (blue). Arrows indicate the LO.

FIG. 3A: Scatter plot showing the log 2 abundance in the LO set and the log 2 ratio between LO and Exo for transcripts with an absolute log 2 fold-change of at least 1 between the LO and Exo mRNA sets. Genes validated by qRT-PCR are highlighted, with genes found to be of higher abundance in LO labelled in red, and genes found to be of lower abundance in LO labelled in blue. FIG. 3B: Validation of mRNA abundance differences between LO and Exo mRNA fractions. For 11 genes, the RNA-Seq fold-change ranking was validated via Fluidigm qRT-PCR, with a strong correlation between the two methods (r=0.76). Gene ontology (GO) enrichment analysis using FunRich software indicates the cellular component (5 out of 6 GO terms show association with membrane structures) FIG. 3C, molecular function FIG. 3D and biological pathways FIG. 3E for the mRNAs overrepresented in LO. 2 out of 3 and 3 out of 5 GO terms respectively associated with transporter or receptor functions. For each GO category the plots show, on the x-axis, the percentage of genes that belong to the GO term indicated in the y-axis. Only statistically significant enrichment is displayed (Bonferroni corrected; * for p<0.05, ** for p<0.001), and the numbers below the asterisks indicate the number of genes for each GO term. mRNA expression of the genes in the selected GO term "Beta 3 integrin cell surface interactions" were analysed using Oncomine database. Gene overexpressed (red) or downregulated (blue) in brain cancer (GBM) vs normal brain are shown. FC=fold change; FIG. 3F: VEGFR mRNA levels were measured by qRT-PCR in HUVEC cells at baseline or after treatment with LO at the indicated time points (*p<0.05).

FIG. 4A: The EV signature (depletion of signal peptide encoding mRNAs, enrichment of E2F4 targets and enrichment of histones) was recapitulated in vivo in EVs isolated from 2 out of 3 patients with invasive lobular carcinoma (ILC) versus control individuals. FIG. 4B: The histogram on the left shows the number of transcripts that are enriched or depleted of at least 2 fold (Log 2) in EVs from all breast cancer patients in comparison with controls. The pie chart shows the distribution of the mRNAs that we found upregulated in plasma EVs in TCGA breast cancer tissues. The size of each slice is determined by the number of transcripts that are enriched in given fractions of patients. 15 mRNAs were altered in 0-1% of the cases, 19 in 2-3% of the cases, 53 in 4-5% of the cases, 46 in 6-9% of the cases, 22 in >10% of the cases. FIG. 4C:

Figure 1A:
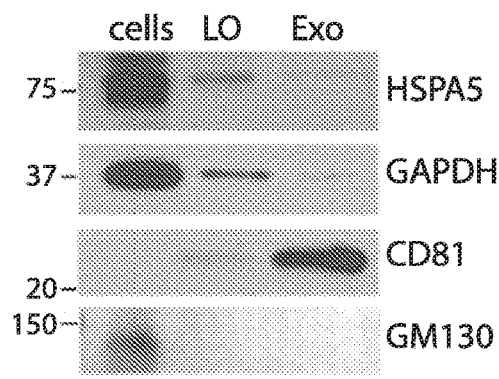
FIG. 1A-FIG. 1H depicts in accordance with various embodiments of the invention, that the mRNA profile of U87 EVs and cells are significantly different. mRNA was isolated from U87 exosomes (Exo), large oncosomes (LO), and U87 cells, and was profiled by RNA-Seq.

CENPF Log 2 expression (FPKM) in plasma EVs from patients (n=15) versus healthy controls (n=5).

FIG. 5A-FIG. 5G depict, in various embodiments of the invention, correlation between cytosol and cell mRNA in ENCODE cell types.

DETAILED DESCRIPTION

All references cited herein are incorporated by reference in their entirety as though fully set forth. Unless defined otherwise, technical and scientific terms used herein have the same meaning as commonly understood by one of ordinary skill in the art to which this invention belongs. Allen et al., *Remington: The Science and Practice of Pharmacy* 22$^{nd}$ ed., Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* 3$^{rd}$ ed., revised ed., J. Wiley & Sons (New York, N.Y. 2006); Smith, *March's Advanced Organic Chemistry Reactions, Mechanisms and Structure* 7$^{th}$ ed., J. Wiley & Sons (New York, N.Y. 2013); Singleton, *Dictionary of DNA and Genome Technology* 3$^{rd}$ ed., Wiley-Blackwell (Nov. 28, 2012); and Green and Sambrook, *Molecular Cloning: A Laboratory Manual* 4th ed., Cold Spring Harbor Laboratory Press (Cold Spring Harbor, N.Y. 2012), provide one skilled in the art with a general guide to many of the terms used in the present application. For references on how to prepare antibodies, see Greenfield, *Antibodies A Laboratory Manual* 2$^{nd}$ ed., Cold Spring Harbor Press (Cold Spring Harbor N.Y., 2013); Köhler and Milstein, *Derivation of specific antibody-producing tissue culture and tumor lines by cell fusion*, Eur. J. Immunol. 1976 July, 6(7):511-9; Queen and Selick, *Humanized immunoglobulins*, U.S. Pat. No. 5,585,089 (1996 December); and Riechmann et al., *Reshaping human antibodies for therapy*, Nature 1988 Mar. 24, 332(6162):323-7.

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

As used herein the term "comprising" or "comprises" is used in reference to compositions, methods, systems, articles of manufacture, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

"Optional" or "optionally" means that the subsequently described circumstance may or may not occur, so that the description includes instances where the circumstance occurs and instances where it does not.

"Beneficial results" may include, but are in no way limited to, lessening or alleviating the severity of the disease condition, preventing the disease condition from worsening, curing the disease condition, preventing the disease condition from developing, lowering the chances of a patient developing the disease condition and prolonging a patient's life or life expectancy. In some embodiments, the disease condition is cancer.

"Cancer" and "cancerous" refer to or describe the physiological condition in mammals that is typically characterized by unregulated cell growth. Examples of cancer include, but are not limited to B-cell lymphomas (Hodgkin's lymphomas and/or non-Hodgkins lymphomas), brain tumor, breast cancer, colon cancer, lung cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, brain cancer, and prostate cancer, including but not limited to androgen-dependent prostate cancer and androgen-independent prostate cancer.

"Chemotherapeutic drugs" or "chemotherapeutic agents" as used herein refer to drugs used to treat cancer including but not limited to Albumin-bound paclitaxel (nab-paclitaxel), Actinomycin, Alitretinoin, All-trans retinoic acid, Azacitidine, Azathioprine, Bevacizumab, Bexatotene, Bleomycin, Bortezomib, Carboplatin, Capecitabine, Cetuximab, Cisplatin, Chlorambucil, Cyclophosphamide, Cytarabine, Daunorubicin, Docetaxel, Doxifluridine, Doxorubicin, Epirubicin, Epothilone, Erlotinib, Etoposide, Fluorouracil, Gefitinib, Gemcitabine, Hydroxyurea, Idarubicin, Imatinib, Ipilimumab, Irinotecan, Mechlorethamine, Melphalan, Mercaptopurine, Methotrexate, Mitoxantrone, Ocrelizumab, Ofatumumab, Oxaliplatin, Paclitaxel, Panitumab, Pemetrexed, Rituximab, Tafluposide, Teniposide, Tioguanine, Topotecan, Tretinoin, Valrubicin, Vemurafenib, Vinblastine, Vincristine, Vindesine, Vinorelbine, Vorinostat, Romidepsin, 5-fluorouracil (5-FU), 6-mercaptopurine (6-MP), Cladribine, Clofarabine, Floxuridine, Fludarabine, Pentostatin, Mitomycin, ixabepilone, Estramustine, or a combination thereof.

The term "extracellular vesicles (EV)" as used herein include any vesicles that are shed by the cells of any living organisms (for example, humans). EVs include but are not limited to exosomes, which are about 20 nm to about 80 nm in size, large oncosomes which are about 1 μm to about 30 μm in size (with a predominance of vesicles of around 3-4 μm) and microvesicles which are about 0.5 to 1 mm in size.

"Isolated" or "purified" large oncosomes as used herein refers to large oncosomes that are not in their natural milieu. No particular level of purification is required. For example, an isolated large oncosome may be removed from its native or natural environment.

"Large Oncosomes" as used herein refer to tumor-derived extracellular vesicles that transmit signaling complexes between cell and tissue compartments. Large oncosomes are about 1 μm to about 30 μm in size. In some embodiments, large oncosomes are shed by amoeboid tumor cells. Large oncosomes comprise lipids, nucleic acids and proteins, each or a combination of which may be used to detect and/or quantify large oncosomes. In various embodiments, the size of the large oncosomes may be about 1 μm to 30 μm, about 5 μm to 30 μm, about 10 μm to 30 μm, about 15 μm to 30 μm, about 20 μm to 30 μm or about 25 μm to 30 μm.

The term "sample" or "biological sample" as used herein denotes a sample taken or isolated from a biological organism, e.g., a tissue sample from a subject. The tissue sample may or may not be maintained under "life" sustaining conditions in vitro for an extended to unlimited period of time. Exemplary samples or biological samples include, but are not limited to, cell sample; tissue sample; tissue; tumor sample; and/or tumor biopsy, whole blood, blood, serum; plasma; cheek swab; mucus; urine; saliva; semen; lymph; fecal extract; sputum; other body fluid or biofluid, etc. or any sample or biological sample. The term also includes a mixture of the above-mentioned samples. The term "sample" also includes untreated or pretreated (or pre-processed) biological samples. In some embodiments the sample is tissue or blood.

The terms "body fluid" or "bodily fluids" are liquids originating from inside the bodies of organisms. Bodily fluids include amniotic fluid, aqueous humour, vitreous humour, bile, blood (e.g., serum), breast milk, cerebrospinal fluid, cerumen (earwax), chyle, chyme, endolymph and perilymph, exudates, feces, female ejaculate, gastric acid, gastric juice, lymph, mucus (e.g., nasal drainage and phlegm), pericardial fluid, peritoneal fluid, pleural fluid, pus, rheum, saliva, sebum (skin oil), serous fluid, semen, smegma, sputum, synovial fluid, sweat, tears, urine, vaginal secretion, and vomit. Extracellular bodily fluids include intravascular fluid (blood plasma), interstitial fluids, lymphatic fluid and transcellular fluid. "Biological sample" also includes a mixture of the above-mentioned body fluids. "Biological samples" may be untreated or pretreated (or pre-processed) biological samples.

Sample collection procedures and devices known in the art are suitable for use with various embodiment of the present invention. Examples of sample collection procedures and devices include but are not limited to: phlebotomy tubes (e.g., a vacutainer blood/specimen collection device for collection and/or storage of the blood/specimen), dried blood spots, Microvette CB300 Capillary Collection Device (Sarstedt), HemaXis blood collection devices (microfluidic technology, Hemaxis), Volumetric Absorptive Microsampling (such as CE-IVD Mitra microsampling device for accurate dried blood sampling (Neoteryx), HemaSpot™-HF Blood Collection Device; a tissue sample collection device.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, and canine species, e.g., dog, fox, wolf. The terms, "patient", "individual" and "subject" are used interchangeably herein. In an embodiment, the subject is mammal. The mammal can be a human, non-human primate, mouse, rat, dog, cat, horse, or cow, but are not limited to these examples. In addition, the methods described herein can be used to treat domesticated animals and/or pets. In various embodiments, the subject is mouse or mice. In various embodiments, the subject is human.

The term "diagnosis," or "dx," refers to the identification of the nature and cause of a certain phenomenon. As used herein, a diagnosis typically refers to a medical diagnosis, which is the process of determining which disease or condition explains a symptoms and signs. A diagnostic procedure, often a diagnostic test or assay, can be used to provide a diagnosis. A diagnosis can comprise detecting the presence of a disease or disorder, or condition.

The term "prognosis," or "px," as used herein refers to predicting the likely outcome of a current standing. For example, a prognosis can include the expected duration and course of a disease or disorder, such as progressive decline or expected recovery.

The term "theranosis," or "tx" as used herein refers to a diagnosis or prognosis used in the context of a medical treatment. For example, theranostics can include diagnostic testing used for selecting appropriate and optimal therapies (or the inverse) based on the context of genetic content or other molecular or cellular analysis. Theranostics includes pharmacogenomics, personalized and precision medicine.

As used herein, the term "administering," refers to the placement of an agent as disclosed herein into a subject by a method or route which results in at least partial localization of the agents at a desired site.

"Patient outcome" refers to whether a patient survives or dies as a result of treatment. A more accurate prognosis for patients as provided in this invention increases the chances of patient survival.

"Poor Prognosis" means that the prospect of survival and recovery of disease is unlikely despite the standard of care for the treatment of the cancer (for example, prostate cancer), that is, surgery, radiation, chemotherapy. Poor prognosis is the category of patients whose survival is less than that of the median survival.

"Good Prognosis" means that the prospect of survival and recovery of disease is likely with the standard of care for the treatment of the disease, for example, surgery, radiation, chemotherapy. Good prognosis is the category of patients whose survival is not less than that of the median survival.

A "recurrence" means that the cancer has returned after initial treatment.

"Non-recurrent" or "recurrence-free", as used herein means that the cancer is in remission; being recurrent means that the cancer is growing and/or has metastasized, and some surgery, therapeutic intervention, and/or cancer treatment is required to lower the chance of lethality. The "non-recurrent subjects" are subjects who have non-recurrent or recurrence-free disease, and they can be used as the control for recurrent subjects who have recurrent disease or recurrence.

"Subject" or "individual" or "animal" or "patient" or "mammal," is meant any subject, particularly a mammalian subject, for whom diagnosis, prognosis, or therapy is desired. In some embodiments, the subject has cancer. In some embodiments, the subject had cancer at some point in the subject's lifetime. In various embodiments, the subject's cancer is in remission, is re-current or is non-recurrent.

"Mammal" as used herein refers to any member of the class Mammalia, including, without limitation, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and so on. In certain embodiments, the mammal is a human subject. The term does not denote a particular age or sex. Thus, adult and newborn subjects, as well as fetuses, whether male or female, are intended to be included within the scope of this term.

"Treatment" and "treating," as used herein refer to both therapeutic treatment and prophylactic or preventative measures, wherein the object is to prevent or slow down (lessen) the targeted pathologic condition, prevent the pathologic condition, pursue or obtain beneficial results, or lower the chances of the individual developing the condition even if the treatment is ultimately unsuccessful. Those in need of treatment include those already with the condition as well as those prone to have the condition or those in whom the condition is to be prevented. Examples of cancer treatment include, but are not limited to, active surveillance, observation, surgical intervention, chemotherapy, immunotherapy, radiation therapy (such as external beam radiation, stereotactic radiosurgery (gamma knife), and fractionated stereotactic radiotherapy (FSR)), focal therapy, systemic therapy, vaccine therapies, viral therapies, molecular targeted therapies, or a combination thereof.

"Tumor," as used herein refers to all neoplastic cell growth and proliferation, whether malignant or benign, and all pre-cancerous and cancerous cells and tissues.

"Therapeutic agents" as used herein refers to agents that are used to, for example, treat, inhibit, prevent, mitigate the effects of, reduce the severity of, reduce the likelihood of developing, slow the progression of and/or cure, a disease. Diseases targeted by the therapeutic agents include cancer.

Extracellular vesicles (EVs) contain a wide range of RNA types with a reported prevalence of noncoding RNA. To date a comprehensive characterization of the protein coding transcripts in EVs is still lacking. We performed RNA-Sequencing (RNA-Seq) of two EV populations and identified a small fraction of transcripts that were expressed at significantly different levels in large oncosomes and exosomes, suggesting they may mediate specialized functions. However, these two EV populations exhibited a common mRNA signature that, in comparison to their donor cells, was significantly enriched in mRNAs encoding E2F transcriptional targets and histone proteins. These mRNAs are primarily expressed in the S-phase of the cell cycle, suggesting that they may be packaged into Evs during S-phase. In silico analysis using subcellular compartment transcriptome data from the ENCODE cell line compendium revealed that EV mRNAs originate from a cytoplasmic RNA pool. The EV signature was independently identified in plasma of patients with breast cancer by RNA-Seq. Furthermore, several transcripts differentially expressed in EVs from patients versus controls mirrored differential expression between normal and breast cancer tissues. Altogether, this largest high-throughput profiling of EV mRNA demonstrates that EVs carry tumor-specific alterations and can be interrogated as a source of cancer-derived cargo.

The inventors find that E2F targets and histone proteins are enriched in EVs (both large oncosomes and exosomes) isolated from glioblastoma cell lines in comparison to their expression in the cell of origin. Additional in silico analysis of the ENCODE compendium that contains expression data on different subcellular fractions of various malignant and benign cell lines, demonstrated that the profile of EVs is similar to the profile of the cytosol, suggesting that most of the RNA exported in EVs derives from the cytosol. Additionally the signature of an enrichment in E2F targets and histones was confirmed in many different cancer cells of various histotypes suggesting that presence of histones and E2F targets are cancer biomarkers in extracellular vesicles isolated from a subject having or suspected of having cancer.

Accordingly, provided herein is a method for diagnosing cancer in a subject in need thereof. The method includes obtaining a sample from a subject desiring diagnosis of cancer, isolating extracellular vesicles from the sample and detecting expression of one or more or all of histone-encoding genes described herein and any one or more or all of genes encoding E2F targets described herein in the extracellular vesicles, wherein an increase in expression in any one or more or all of histone-encoding genes and genes encoding E2F targets relative to a reference value is indicative of cancer in a subject. In some embodiments, the histone proteins are any one or more or all of members of histone H1 family. In some embodiments, the histone proteins are any one or more or all of members of histone H2A family. In some embodiments, the histone proteins are any one or more or all of members of histone H2B family. In some embodiments, the histone proteins are any one or more or all of members of histone H3 family. In some embodiments, the histone proteins are any one or more or all of members of histone H4 family. In some embodiments, the histones genes are any one or more or all of HIST1H3F, HIST1H3G, HIST1H2AJ, HIST1H2BM, HIST1H1B, HIST1H3B, HIST1H2AH, HIST1H3J, HIST1H2BI, HIST1H2BO and HIST1H2AI. In some embodiments, the E2F targets are any one or more or all of SPC24, CENPF, ARHGAP11B, CEP128, QPCTL, HMMR, HIST1H2BL, NDC80, KIF15, HMBS, ABCB6, HIST1H2BM, GUCY1B3, SYNGR4, RECQL4, CDCA7, TTK, CKAP2, BORA and CENPW genes. The method further comprises selecting or prescribing therapy for cancer to subjects diagnosed with having cancer. In one embodiment, the extracellular vesicles are exosomes. In another embodiment, the extracellular vesicles are large oncosomes. In a further embodiment, the extracellular vesicles are microvesicles. In a further embodiment, the extracellular vesicles are a combination of microvesicles, large oncosomes and exosomes. In some embodiments, the method further comprises referring the subject to one or more cancer specialists. In some embodiments the cancer specialist is selected from a medical oncologist, radiation oncologist, surgical oncologist, psycho-oncologist, hematologist-oncologist, gynecologic oncologist, and pediatric oncologist Provided herein is a method for diagnosing glioblastoma in a subject in need thereof. The method includes obtaining a sample from a subject having or suspected of having cancer, isolating extracellular vesicles from the sample and detecting the expression of any one or more or all of UBC, HIST1H3F, HIST1H3G, HIST1H2AJ, HIST1H2BM, HIST1H1B, UBE2C, TK1, MYBL2, HIST1H3B, HIST1H2AH, RRM2, HIST1H3J, HIST1H2BI, HIST1H2BO, HIST1H2AI, ANLN, ARHGAP11A, RAB13 and ZWINT genes in the extracellular vesicles, wherein an increased expression of any one or more or all of the UBC, HIST1H3F, HIST1H3G, HIST1H2AJ, HIST1H2BM, HIST1H1B, UBE2C, TK1, MYBL2, HIST1H3B, HIST1H2AH, RRM2, HIST1H3J, HIST1H2BI, HIST1H2BO, HIST1H2AI, ANLN, ARHGAP11A, RAB13 and ZWINT genes relative to a reference value is indicative of glioblastoma in the subject. The method further comprises selecting or prescribing therapy for glioblastoma to subjects diagnosed with having glioblastoma. In one embodiment, the extracellular vesicles are exosomes. In another embodiment, the extracellular vesicles are large oncosomes. In a further embodiment, the extracellular vesicles are microvesicles. In a further embodiment, the extracellular vesicles are a combination of microvesicles, large oncosomes and exosomes. In some embodiments, the method further comprises referring the subject to one or more cancer specialists. In some embodiments the cancer specialist is selected from a medical oncologist, radiation oncologist, surgical oncologist, psycho-oncologist, hematologist-oncologist, gynecologic oncologist, and pediatric oncologist.

Also provided herein is a method for diagnosing glioblastoma in a subject in in need thereof. The method includes obtaining results of expression levels of any one or more or all of UBC, HIST1H3F, HIST1H3G, HIST1H2AJ, HIST1H2BM, HIST1H1B, UBE2C, TK1, MYBL2, HIST1H3B, HIST1H2AH, RRM2, HIST1H3J, HIST1H2BI, HIST1H2BO, HIST1H2AI, ANLN, ARHGAP11A, RAB13 and ZWINT genes in extracellular vesicles isolated from a sample obtained from a subject desiring diagnosis and determining that the subject has a glioblastoma if increased expression of any one or more or all of UBC, HIST1H3F, HIST1H3G, HIST1H2AJ, HIST1H2BM, HIST1H1B, UBE2C, TK1, MYBL2, HIST1H3B, HIST1H2AH, RRM2, HIST1H3J, HIST1H2BI, HIST1H2BO, HIST1H2AI, ANLN, ARHGAP11A, RAB13 and ZWINT genes relative to a reference value is detected. The method further comprises selecting or prescribing cancer therapy to subjects diagnosed with having glioblastoma. In one embodiment, the extracellular vesicles are exosomes. In another embodiment, the extracellular vesicles are large oncosomes. In a further embodiment, the extracellular vesicles are microvesicles. In a further embodiment, the extracellular vesicles are a combination of microvesicles, large oncosomes and exosomes. In some embodiments, the method further comprises referring the subject to one or more cancer specialists. In some embodiments the cancer specialist is selected from a medical oncologist, radiation oncologist, surgical oncologist, psycho-oncologist, hematologist-oncologist, gynecologic oncologist, and pediatric oncologist.

Further provide herein is a method for diagnosing breast cancer in a subject in need thereof. The method includes obtaining a sample from a subject having or suspected of having cancer, isolating extracellular vesicles from the sample and detecting the expression of any one or more or all of NXF3, LOC650293, PAM16, PRB2, ANP32c, KRTAP10-12, APOBEC3H, SPC24, PRB4, LHB, S100A3 and SSX7 genes in the extracellular vesicles, wherein an increased expression of any one or more or all of the NXF3, LOC650293, PAM16, PRB2, ANP32c, KRTAP10-12, APOBEC3H, SPC24, PRB4, LHB, S100A3 and SSX7 genes relative to a reference value is indicative of increased likelihood of breast cancer in the subject. The method further comprises selecting or prescribing breast cancer therapy to subjects diagnosed with having breast cancer. In one embodiment, the extracellular vesicles are exosomes. In another embodiment, the extracellular vesicles are large oncosomes. In a further embodiment, the extracellular vesicles are microvesicles. In a further embodiment, the extracellular vesicles are a combination of microvesicles, large oncosomes and exosomes. In some embodiments, the method further comprises referring the subject to one or more cancer specialists. In some embodiments the cancer specialist is selected from a medical oncologist, radiation oncologist, surgical oncologist, psycho-oncologist, hematologist-oncologist, gynecologic oncologist, and pediatric oncologist.

Also provide herein is a method for diagnosing breast cancer in a subject in need thereof. The method includes obtaining results of expression levels of any one or more or all of NXF3, LOC650293, PAM16, PRB2, ANP32c, KRTAP10-12, SPC24, PRB4, LHB, S100A3 and SSX7 genes in extracellular vesicles isolated from a sample obtained from a subject and determining that the subject has an increased likelihood of breast cancer if increased expression of any one or more or all of NXF3, LOC650293, PAM16, PRB2, ANP32c, KRTAP10-12, SPC24, PRB4, LHB, S100A3 and SSX7 genes relative to a reference value is detected. The method further comprises selecting or prescribing breast cancer therapy to subjects diagnosed with having breast cancer. In one embodiment, the extracellular vesicles are exosomes. In another embodiment, the extracellular vesicles are large oncosomes. In a further embodiment, the extracellular vesicles are microvesicles. In a further embodiment, the extracellular vesicles are a combination of microvesicles, large oncosomes and exosomes. In some embodiments, the method further comprises referring the subject to one or more cancer specialists. In some embodiments the cancer specialist is selected from a medical oncologist, radiation oncologist, surgical oncologist, psycho-oncologist, hematologist-oncologist, gynecologic oncologist, and pediatric oncologist.

Further provide herein is a method for diagnosing invasive lobular carcinoma (ILC) in a subject in need thereof. The method includes obtaining a sample from a subject having or suspected of having cancer, isolating extracellular vesicles from the sample and detecting the expression of any one or more or all of KRTAP6-1, HBG1, AHSP, SPC24, HBE1, KCNH2, SLC43A1, CENPF, KRTAP13-3, MT1A, FHDC1, SMR3A, SPTA1, CA1 and TSPO2 genes in the extracellular vesicles, wherein an increased expression of any one or more or all of the KRTAP6-1, HBG1, AHSP, SPC24, HBE1, KCNH2, SLC43A1, CENPF, KRTAP13-3, MT1A, FHDC1, SMR3A, SPTA1, CA1 and TSPO2 genes relative to a reference value is indicative of increased likelihood of ILC in the subject. The method further comprises selecting or prescribing ILC therapy to subjects diagnosed with having ILC. In one embodiment, the extracellular vesicles are exosomes. In another embodiment, the extracellular vesicles are large oncosomes. In a further embodiment, the extracellular vesicles are microvesicles. In a further embodiment, the extracellular vesicles are a combination of microvesicles, large oncosomes and exosomes. In some embodiments, the method further comprises referring the subject to one or more cancer specialists. In some embodiments the cancer specialist is selected from a medical oncologist, radiation oncologist, surgical oncologist, psycho-oncologist, hematologist-oncologist, gynecologic oncologist, and pediatric oncologist.

Also provide herein is a method for diagnosing ILC in a subject in need thereof. The method includes obtaining results of expression levels of any one or more or all of KRTAP6-1, HBG1, AHSP, SPC24, HBE1, KCNH2, SLC43A1, CENPF, KRTAP13-3, MT1A, FHDC1, SMR3A, SPTA1, CA1 and TSPO2 genes in extracellular vesicles isolated from a sample obtained from a subject and determining that the subject has an increased likelihood of ILC if increased expression of any one or more or all of KRTAP6-1, HBG1, AHSP, SPC24, HBE1, KCNH2, SLC43A1, CENPF, KRTAP13-3, MT1A, FHDC1, SMR3A, SPTA1, CA1 and TSPO2 genes relative to a reference value is detected. The method further comprises selecting or prescribing ILC therapy to subjects diagnosed with having ILC. In one embodiment, the extracellular vesicles are exosomes. In another embodiment, the extracellular vesicles are large oncosomes. In a further embodiment, the extracellular vesicles are microvesicles. In a further embodiment, the extracellular vesicles are a combination of microvesicles, large oncosomes and exosomes. In some embodiments, the method further comprises referring the subject to one or more cancer specialists. In some embodiments the cancer specialist is selected from a medical oncologist, radiation oncologist, surgical oncologist, psycho-oncologist, hematologist-oncologist, gynecologic oncologist, and pediatric oncologist.

Also provide herein is a method for diagnosing ILC in a subject in need thereof. The method includes obtaining results of expression levels of any one or more or all of SPC24, CENPF, HMBS, KIF15, HIST1H2BM, HIST1H2BL, NDC80, HMMR, HIST1H3C, HIST1H2BB, TTK, TYMS, RRM2, HIST1H2AH, DLGAP5, MKI67, HIST1H3G, PRC1 and HIST1H2AJ genes in extracellular vesicles isolated from a sample obtained from a subject and determining that the subject has an increased likelihood of ILC if increased expression of any one or more or all of KRTAP6-1, HBG1, AHSP, SPC24, HBE1, KCNH2, SLC43A1, CENPF, KRTAP13-3, MT1A, FHDC1, SMR3A, SPTA1, CA1 and TSPO2 genes relative to a reference value is detected. The method further comprises selecting or prescribing ILC therapy to subjects diagnosed with having ILC. In one embodiment, the extracellular vesicles are exosomes. In another embodiment, the extracellular vesicles are large oncosomes. In a further embodiment, the extracellular vesicles are microvesicles. In a further embodiment, the extracellular vesicles are a combination of microvesicles, large oncosomes and exosomes. In some embodiments, the method further comprises referring the subject to one or more cancer specialists. In some embodiments the cancer specialist is selected from a medical oncologist, radiation oncologist, surgical oncologist, psycho-oncologist, hematologist-oncologist, gynecologic oncologist, and pediatric oncologist Also provide herein is a method for diagnosing ILC in a subject in need thereof. The method includes obtaining results of expression levels of any one or more or all of SPC24, CENPF, HMBS, KIF15, HIST1H2BM, HIST1H2BL, NDC80, HMMR, HIST1H3C, HIST1H2BB, TTK, TYMS, RRM2, HIST1H2AH, DLGAP5, MKI67, HIST1H3G, PRC1 and HIST1H2AJ genes in extracellular vesicles isolated from a sample obtained from a subject and determining that the subject has an increased likelihood of ILC if increased expression of any one or more or all of SPC24, CENPF, HMBS, KIF15, HIST1H2BM, HIST1H2BL, NDC80, HMMR, HIST1H3C, HIST1H2BB, TTK, TYMS, RRM2, HIST1H2AH, DLGAP5, MKI67, HIST1H3G, PRC1 and HIST1H2AJ genes relative to a reference value is detected. The method further comprises selecting or prescribing ILC therapy to subjects diagnosed with having ILC. In one embodiment, the extracellular vesicles are exosomes. In another embodiment, the extracellular vesicles are large oncosomes. In a further embodiment, the extracellular vesicles are microvesicles. In some embodiments, the method further comprises referring the subject to one or more cancer specialists. In some embodiments the cancer specialist is selected from a medical oncologist, radiation oncologist, surgical oncologist, psycho-oncologist, hematologist-oncologist, gynecologic oncologist, and pediatric oncologist.

In some embodiments, the sample is blood or tissue.

Detection of Extracellular Vesicles

As described herein, the determination of likelihood of cancer (for example, glioblastoma, breast cancer or invasive lobular carcinoma) in a subject and/or treatment of cancer in a subject (for example, glioblastoma, breast cancer or invasive lobular carcinoma) includes detecting and/or quantifying extracellular vesicles in samples obtained from the subject. In various embodiments, the samples are blood, tissue or a combination thereof.

Further, as described herein, extracellular vesicles comprise lipids, nucleic acid and proteins (collectively terms the "molecular content"), each of which or a combination thereof may be used to not only detect and/or quantify extracellular vesicles but may also be used to identify the type of cancer that may be metastasizing.

The nucleic acid component of the molecular content of extracellular vesicles includes DNA and/or variants thereof such as single-stranded DNA (ssDNA), double-stranded DNA (dsDNA), cDNA and/or genomic DNA. The nucleic acid component of the molecular content of extracellular vesicles also includes RNA and its variants including but not limited to mRNA, rRNA, tRNA, siRNA, miRNA and/or non-coding RNA. The nucleic acid component of the molecular content of extracellular vesicles also includes tandem repeats (such as satellite DNA/RNA, microsatellite DNA/RNA or minisatellite DNA/RNA), interspersed repeats (such as transposons (transposable elements), Short Interspersed Nuclear Elements (SINEs, such as Alu's), Long Interspersed Nuclear Elements (LINEs such LINE-1), global direct repeats, local direct simple repeats, local direct repeats, local direct repeats with spacer and/or endogenous retroviruses (endogenous viral elements).

Polypeptides may be modified or unmodified. Modifications to the polypeptides include but are not limited to any one or more of myristoylation, palmitoylation, prenylation, farnesylation, geranylgeranylation, glypiation, glycosylphosphatidylinositol (GPI) lipoylation, addition of flavin moiety (FMN or FAD), addition of heme C, phosphopantetheinylation, diphthamide formation, addition of ethanolamine phosphoglycerol, hypusine formation, acylation, alkylation, amide bond formation, butyrylation, gamma-carboxylation, glycosylation, hydroxylysine, polysialylation, malonylation, hydroxylation, iodination, nucleotide addition (such as ADP-ribosylation), oxidation, phosphate ester (O-linked) or phosphoramidate (N-linked) formation, phosphorylation, adenylylation, propionylation, pyroglutamate formation, S-glutathionylation, S-nitrosylation, Succinylation, sulfation, selenoylation, ISGylation, SUMOylation, ubiquitination, Neddylation, Pupylation, citrullination, deamidation, eliminylation, carbamylation, disulfide bridges formation, proteolytic cleavage, racemization or a combination thereof.

The lipid component of the molecular content of the extracellular vesicles (including microvesicles, exosomes and large oncosomes) includes but is not limited to any one or more of fatty acids, glycerolipids, glycerophospholipids, sphingolipids, sterol lipids, prenol lipids, saccharolipids, polyketides, phosphoglycerides, glycolipids, or a combination thereof.

Extracellular vesicles may be isolated from biological material including but not limited to any one or more of tissue, cells, blood, plasma, serum, urine, sputum, spinal fluid, pleural fluid, nipple aspirate, lymph fluid, fluid of the respiratory tract, fluid of the intestinal tract, fluid of the genitourinary tract, fluid of the lymphatic system, semen, cerebrospinal fluid, tears, saliva, intra-organ system fluid, tumor cyst fluid, amniotic fluid or a combination thereof.

In some embodiments, extracellular vesicles are purified from a sample obtained from a subject and detected and/or quantified without labeling the extracellular vesicles. In an embodiment, unlabeled extracellular vesicles may be quantified using flow cytometry techniques, for example, using forward scatter flow cytometry. In an embodiment, forward scatter flow cytometry is used with 1 µm to 10 µm beads to enrich for detection large oncosomes. Methods for performing forward scatter flow cytometry would be apparent to a person of skill in the art and may be performed as described in, for example, Di Vizio et al. (*Cell Cycle*. 2009 August; 8(15):2420-4), Dragovic et al. (*Nanomedicine*. 2011 December; 7(6):780-8), Wysoczynski M and Ratajczak M Z (*Int J Cancer.* 2009 Oct. 1; 125(7):1595-603). Broadly, flow cytometry analysis of extracellular vesicles may be performed by setting forward scatter (FSC) and side scatter (SSC) voltages as low as that the background noise, determined by running double 0.2 µm filtered PBS at the highest flow rate available (in some embodiments, no higher that 0-4 events/second. After data acquisition, extracellular vesicles can be analyzed by setting FSC and SSC on a logarithmic scale.

In some embodiments, the labeled extracellular vesicles may be detected using microfluidic systems as described in Shao et al. (*Nature Medicine* December 2012 Vol 18(12) pages 1835-1841). The methods described in Shao et al. are applied to exosomes but as would be apparent to a person of skill in the art, these methods may be applied to large oncosomes as well. The larger size of the large oncosomes may facilitate better capture of the large oncosomes.

In some embodiments, the isolated/purified extracellular vesicles obtained from a sample from a subject may be labeled and then quantified and/or detected. In such instances, the nucleic acids, lipids and/or proteins in the extracellular vesicles are labeled. In an embodiment, flow cytometry is used to detect and quantify the labeled extracellular vesicles. In an embodiment, extracellular vesicles are labeled with antibodies that bind to specific proteins of interest.

In further embodiments, the isolated/purified extracellular vesicles may be denatured and the denatured material may be used as an analyte to detect the presence of one or more proteins of interest in the extracellular vesicles. For example, specific antibodies may be used to detect the presence of one or more proteins of interest. Any suitable immunoassay method may be utilized, including those which are commercially available, to ascertain the presence of, and optionally quantify the amount of, the protein of interest present in the analyte. The presence (and optionally the amount) of the protein of interest in the analyte is indicative of the presence of said protein in the extracellular vesicles. In various embodiments, the proteins of interest may be the cancer specific markers, including but not limited to the markers described herein. In various embodiments, the antibody is any one or more of a monoclonal antibody or fragment thereof, a polyclonal antibody or a fragment thereof, chimeric antibodies, humanized antibodies, human antibodies, and a single chain antibody. Extensive discussion of the known immunoassay techniques is not required here since these are known to those of skill in the art. Typical suitable immunoassay techniques include Western blots, sandwich ELISA, radioimmunoassays (RIA), competitive binding assays, homogeneous assays, heterogeneous assays, etc. Various known immunoassay methods are reviewed, e.g., in *Methods in Enzymology,* 70, pp. 30-70 and 166-198 (1980).

Further, "sandwich-type" assays may be used with the methods described herein. Some examples of sandwich-type assays are described in U.S. Pat. No. 4,168,146 and U.S. Pat. No. 4,366,241. Alternatively, "competitive-type" assays may be used with the methods described herein. In a competitive assay, the labeled probe is generally conjugated with a molecule that is identical to, or an analog of, the analyte. Thus, the labeled probe competes with the analyte of interest for the available receptive material. Competitive assays are typically used for detection of analytes such as haptens, each hapten being monovalent and capable of binding only one antibody molecule. Examples of competitive immunoassay devices are described in U.S. Pat. Nos. 4,235,601, 4,442,204 and 5,208,535.

Antibodies, that may be used to detect one or more proteins of interest in extracellular vesicles, may be labeled. In some embodiments, the detection antibody is labeled by covalently linking to an enzyme, labeled with a fluorescent compound or metal or is labeled with a chemiluminescent compound. For example, the detection antibody can be labeled with catalase and the conversion uses a colorimetric substrate composition comprises potassium iodide, hydrogen peroxide and sodium thiosulphate; the enzyme can be alcohol dehydrogenase and the conversion uses a colorimetric substrate composition comprises an alcohol, a pH indicator and a pH buffer, wherein the pH indicator is neutral red and the pH buffer is glycine-sodium hydroxide; the enzyme can also be hypoxanthine oxidase and the conversion uses a colorimetric substrate composition comprises xanthine, a tetrazolium salt and 4,5-dihydroxy-1,3-benzene disulphonic acid. In one embodiment, the detection antibody is labeled by covalently linking to an enzyme, label with a fluorescent compound or metal, or label with a chemiluminescent compound.

Direct and indirect labels can be used in immunoassays. A direct label can be defined as an entity, which in its natural state, is visible either to the naked eye or with the aid of an optical filter and/or applied stimulation, e.g., ultraviolet light, to promote fluorescence. Examples of colored labels which can be used include metallic sol particles, gold sol particles, dye sol particles, dyed latex particles or dyes encapsulated in liposomes. Other direct labels include radionuclides and fluorescent or luminescent moieties. Indirect labels such as enzymes can also be used according to the invention. Various enzymes are known for use as labels such as, for example, alkaline phosphatase, horseradish peroxidase, lysozyme, glucose-6-phosphate dehydrogenase, lactate dehydrogenase and urease. For a detailed discussion of enzymes in immunoassays see Engvall, Enzyme Immunoassay ELISA and EMIT, Methods of Enzymology, 70, 419-439 (1980).

The antibody can be attached to a surface. Examples of useful surfaces on which the antibody can be attached for the purposes of detecting the desired antigen include nitrocellulose, PVDF, polystyrene, and nylon. The surface or support may also be a porous support (see, e.g., U.S. Pat. No. 7,939,342). The assays can be carried out in various assay device formats including those described in U.S. Pat. Nos. 4,906,439; 5,051,237 and 5,147,609 to PB Diagnostic Systems, Inc.

In some embodiments of the processes and methods described herein, detecting the presence and/or level of antibodies reactive to cancer specific markers (for examples, cancer specific proteins) present in extracellular vesicles includes contacting the isolated extracellular vesicles from the cancer patient with an antibody or a fragment thereof that specifically binds to the cancer specific marker of interest, forming an antibody-protein complex between the antibody and marker present in the sample, washing the sample to remove the unbound antibody, adding a detection antibody that is labeled and is reactive to the antibody bound to marker in the sample, washing to remove the unbound labeled detection antibody and converting the label to a detectable signal, wherein the detectable signal is indicative of the presence and/or level of the cancer specific marker in the sample from the patient. In some embodiments, the effector component is a detectable moiety selected from the group consisting of a fluorescent label, a radioactive compound, an enzyme, a substrate, an epitope tag, electron-dense reagent, biotin, digonigenin, hapten and a combination thereof. In some embodiments, the detection antibody is labeled by covalently linking to an enzyme, labeled with a fluorescent compound or metal, labeled with a chemiluminescent compound. The level of the marker may be obtained by measuring a light scattering intensity resulting from the formation of an antibody-protein complex formed by a reaction of marker in the sample with the antibody, wherein the light scattering intensity of at least 10% above a control light scattering intensity indicates the likelihood of presence of the cancer specific marker and thereby, presence of extracellular vesicles in the sample and increased likelihood of the cancers as described herein.

Techniques that may be used to assess the amount of nucleic acid encoding cancer-specific marker of interest present in the extracellular vesicles isolated from a sample obtained from a subject include but are not limited to in situ hybridization (e.g., Angerer (1987) *Meth. Enzymol* 152: 649). Preferred hybridization-based assays include, but are not limited to, traditional "direct probe" methods such as Southern blots or in situ hybridization (e.g., FISH and FISH plus SKY), and "comparative probe" methods such as comparative genomic hybridization (CGH), e.g., cDNA-based or oligonucleotide-based CGH. The methods can be used in a wide variety of formats including, but not limited to, substrate (e.g. membrane or glass) bound methods or array-based approaches. Probes that may be used for nucleic acid analysis are typically labeled, e.g., with radioisotopes or fluorescent reporters. Preferred probes are sufficiently long so as to specifically hybridize with the target nucleic acid(s) under stringent conditions. The preferred size range is from about 200 bases to about 1000 bases. Hybridization protocols suitable for use with the methods of the invention are described, e.g., in Albertson (1984) *EMBO J.* 3: 1227-1234; Pinkel (1988) *Proc. Natl. Acad. Sci. USA* 85: 9138-9142; EPO Pub. No. 430,402; *Methods in Molecular Biology*, Vol. 33: In situ Hybridization Protocols, Choo, ed., Humana Press, Totowa, N.J. (1994), Pinkel, et al. (1998) *Nature Genetics* 20: 207-211, and/or Kallioniemi (1992) *Proc. Natl Acad Sci USA* 89:5321-5325 (1992).

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis, et al. (1990) PCR Protocols, *A Guide to Methods and Applications*, Academic Press, Inc. N.Y.). Measurement of DNA copy number at microsatellite loci using quantitative PCR analysis is described in Ginzonger, et al. (2000) *Cancer Research* 60:5405-5409. The known nucleic acid sequence for the genes is sufficient to enable one of skill in the art to routinely select primers to amplify any portion of the gene. Fluorogenic quantitative PCR may also be used in the methods of the invention. In fluorogenic quantitative PCR, quantitation is based on amount of fluorescence signals, e.g., TaqMan and sybr green.

Other suitable amplification methods include, but are not limited to, ligase chain reaction (LCR) (see Wu and Wallace (1989) *Genomics* 4: 560, Landegren, et al. (1988) *Science* 241:1077, and Barringer et al. (1990) *Gene* 89: 117), transcription amplification (Kwoh, et al. (1989) *Proc. Natl. Acad. Sci. USA* 86: 1173), self-sustained sequence replication (Guatelli, et al. (1990) *Proc. Nat. Acad. Sci. USA* 87: 1874), dot PCR, and linker adapter PCR, etc.

In certain embodiments, other techniques may be used to determine expression of a polynucleotide gene product, including microarray analysis (Han, M., et al., Nat Biotechnol, 19: 631-635, 2001; Bao, P., et al., *Anal Chem*, 74: 1792-1797, 2002; Schena et al., *Proc. Natl. Acad. Sci. USA* 93:10614-19, 1996; and Heller et al., *Proc. Natl. Acad. Sci. USA* 94:2150-55, 1997) and SAGE (serial analysis of gene expression). Like MPSS, SAGE is digital and can generate a large number of signature sequences. (see e.g., Velculescu, V. E., et al., *Trends Genet*, 16: 423-425., 2000; Tuteja R. and Tuteja N. *Bioessays*. 2004 August; 26(8):916-22), although orders of magnitude fewer than that are available from techniques such as MPSS.

In certain embodiments, the term "microarray" includes a "nucleic acid microarray" having a substrate-bound plurality of nucleic acids, hybridization to each of the plurality of bound nucleic acids being separately detectable. The substrate can be solid or porous, planar or non-planar, unitary or distributed. Nucleic acid microarrays include all the devices so called in Schena (ed.), *DNA Microarrays: A Practical Approach* (Practical Approach Series), Oxford University Press (1999); *Nature Genet.* 21(1) (suppl.): 1-60 (1999); Schena (ed.), *Microarray Biochip: Tools and Technology*, Eaton Publishing Company/BioTechniques Books Division (2000). Nucleic acid microarrays may include a substrate-bound plurality of nucleic acids in which the plurality of nucleic acids are disposed on a plurality of beads, rather than on a unitary planar substrate, as described, for example, in Brenner et al., *Proc. Natl. Acad. Sci. USA* 97(4): 1665-1670 (2000). Examples of nucleic acid microarrays may be found in, for example, U.S. Pat. Nos. 6,391,623, 6,383,754, 6,383, 749, 6,380,377, 6,379,897, 6,376,191, 6,372,431, 6,351,712 6,344,316, 6,316,193, 6,312,906, 6,309,828, 6,309,824, 6,306,643, 6,300,063.

Suitable methods for assaying for the expression of various cancer-specific markers present in isolated extracellular vesicles (for example, non-denatured extracellular vesicles or denatured extracellular vesicles) isolated from samples obtained from subjects include but are not limited to any one or more of DNA sequencing, comparative genomic hybridization (CGH), array CGH (aCGH), SNP analysis, mRNA expression assay, RT-PCR, real-time PCR, or a combination thereof. In various embodiments, the assay for detection of nucleic acids encoding cancer-specific markers or protein levels of cancer-specific markers present in the isolated extracellular vesicles include any one or more of Northern blot analysis, Southern blot analysis, reverse transcription-polymerase chain reaction (RT-PCR), polymerase chain reaction (PCR), enzyme-linked immunosorbent assay (ELISA), radio-immuno assay (MA), sodium dodecyl sulfate polyacrylamide gel electrophoresis (SDS-PAGE), Western blot analysis, mass spectrometry immune assays (MSIA), stable isotope standard capture with anti-peptide antibodies (SISCAPA), two-dimensional electrophoresis, PROTOMAP, which combines SDS-PAGE with shotgun proteomics, matrix-assisted laser desorption/ionization (MALDI), fast parallel proteolysis (FASTpp), yeast two-hybrid analysis, protein microarrays, immunoaffinity chromatography, immunoaffinity chromatography followed by mass spectrometry, dual polarization interferometry, microscale thermophoresis, phage display method, stable isotope labeling by amino acids in cell culture (SILAC) or a combination thereof. In some embodiments, the presence of cancer-specific markers in isolated extracellular vesicles may be ascertained by measuring the substrate upon which the marker may act, such that the substrate serves as a surrogate marker for the cancer specific marker.

In various embodiments, tissue samples obtained from a subject with cancer may be analyzed for extracellular vesicles. Extracellular vesicles in the tissue sample may be identified by staining the tissue using any one or more of hematoxylin and eosin (H&E) stain, Periodic acid-Schiff (PAS) stain, Sudan stain, cytostain, Papanicolaou stain, Nissl stain, azocarmine stain, neutral red or janus green. In further embodiments, the tissue sample may be analyzed by immuno-histochemical staining. Immuno-histochemical staining (IHS) may provide information about the presence, location and distribution of extracellular vesicles that may be bound to the tissue sample or may be present surrounding the tissue sample. Antigens for HIS include proteins, peptides, nucleic acids, small molecules or any other molecule that may be specifically recognized by an antibody. In various embodiments, the antibodies may specifically bind the cancer specific markers described herein. Unbound antibody may be removed by washing. The specifically bound antibody may be detected by treating the bound antibody with, for example a labeled secondary antibody or labeled avidin/streptavidin. Suitable labels for immunohistochemistry include but are not limited to fluorophores such as fluoroscein and rhodamine, enzymes such as alkaline phosphatase and horse radish peroxidase, and radionuclides such as $^{32}P$ and $^{125}I$.

Reference Values

In some embodiments, the reference value is the mean or median number of extracellular vesicles and the molecular content (such as proteins, nucleic acids, lipids) of the extracellular vesicles in a population of subjects that do not have cancer. In such subjects, complete absence of extracellular vesicles may be expected in subjects that do not have cancer.

In some embodiments, the reference value is the mean or median number of extracellular vesicles and the molecular content (such as proteins, nucleic acids, lipids) of the extracellular vesicles in a population of subjects that have cancer in remission.

In an additional embodiment, the reference value is the mean or median number of extracellular vesicles and the molecular content (such as proteins, nucleic acids, lipids) of the extracellular vesicles in one or more samples from the subject desiring diagnosis wherein the one or more samples are obtained at a different (for example, an earlier) time point, such as during diagnosis, before treatment, after treatment or a combination thereof.

Exemplary embodiments of the molecular content of extracellular vesicles include genes described herein, the expression profile of which is used to diagnose cancer.

In various embodiments, the extracellular vesicles isolated from a sample obtained from a subject desiring diagnosis of cancer compared to the reference value is increased by at least or about 10%, 20%, 30%, 40%, 50%, 60%, 70%, 80%, 90% or 100%. In various embodiments, the extracellular vesicles isolated from a sample obtained from a subject desiring diagnosis of cancer compared to the reference value is increased by at least or about 1-fold, 2-fold, 3-fold, 4-fold, 5-fold, 10-fold, 15-fold, 20-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, 100-fold or a combination thereof.

In various embodiments, the expression of genes described herein in the extracellular vesicles isolated from a sample obtained from a subject desiring diagnosis compared to the reference value is increased by at least or about 10%, 20%, 30%, 40%, 50%, 60%, 70%, 80%, 90% or 100%. In various embodiments, the expression of genes described herein in the extracellular vesicles isolated from a sample obtained from a subject desiring diagnosis compared to the reference value is increased by at least or about 1-fold, 2-fold, 3-fold, 4-fold, 5-fold, 10-fold, 15-fold, 20-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, 100-fold or a combination thereof.

Therapies

In accordance with various embodiments of the invention, the therapies that may be prescribed to a subject with increased likelihood of cancer as described herein may be selected, used and/or administered to treat a cancer patient (for example a patient with breast cancer, glioblastoma or invasive lobular carcinoma). In various embodiments, the therapy may be any one or more of surgery, radiation, chemotherapy, immunotherapy, vaccine or combinations thereof.

In some embodiments, chemotherapeutic agents may be selected from any one or more of cytotoxic antibiotics, antimetabolities, anti-mitotic agents, alkylating agents, arsenic compounds, DNA topoisomerase inhibitors, taxanes, nucleoside analogues, plant alkaloids, and toxins; and synthetic derivatives thereof. Exemplary compounds include, but are not limited to, alkylating agents: treosulfan, and trofosfamide; plant alkaloids: vinblastine, paclitaxel, docetaxol; DNA topoisomerase inhibitors: doxorubicin, epirubicin, etoposide, camptothecin, topotecan, irinotecan, teniposide, crisnatol, and mitomycin; anti-folates: methotrexate, mycophenolic acid, and hydroxyurea; pyrimidine analogs: 5-fluorouracil, doxifluridine, and cytosine arabinoside; purine analogs: mercaptopurine and thioguanine; DNA antimetabolites: 2'-deoxy-5-fluorouridine, aphidicolin glycinate, and pyrazoloimidazole; and antimitotic agents: halichondrin, colchicine, and rhizoxin. Compositions comprising one or more chemotherapeutic agents (e.g., FLAG, CHOP) may also be used. FLAG comprises fludarabine, cytosine arabinoside (Ara-C) and G-CSF. CHOP comprises cyclophosphamide, vincristine, doxorubicin, and prednisone. In another embodiments, PARP (e.g., PARP-1 and/or PARP-2) inhibitors are used and such inhibitors are well known in the art (e.g., Olaparib, ABT-888, BSI-201, BGP-15 (N-Gene Research Laboratories, Inc.); INO-1001 (Inotek Pharmaceuticals Inc.); PJ34 (Soriano et al., 2001; Pacher et al., 2002b); 3-aminobenzamide (Trevigen); 4-amino-1,8-naphthalimide; (Trevigen); 6(5H)-phenanthridinone (Trevigen); benzamide (U.S. Pat. Re. 36,397); and NU1025 (Bowman et al.).

In various embodiments, therapies include use of chemotherapeutic agents to treat cancer. Such agents include but are not limited to Abiraterone Acetate, Cabazitaxel, Degarelix, Denosumab, Docetaxel, Enzalutamide, Jevtana (Cabazitaxel), Leuprolide Acetate, Lupron (Leuprolide Acetate), Lupron Depot (Leuprolide Acetate), Lupron Depot-3 Month (Leuprolide Acetate), Lupron Depot-4 Month (Leuprolide Acetate), Lupron Depot-Ped (Leuprolide Acetate), Prednisone, Prolia (Denosumab), Provenge (Sipuleucel-T), Radium 223 Dichloride, Sipuleucel-T, Taxotere (Docetaxel), Viadur (Leuprolide Acetate), Xgeva (Denosumab), Xofigo (Radium 223 Dichloride), Xtandi (Enzalutamide), Zytiga (Abiraterone Acetate) or a combination thereof.

In various embodiments, therapies include, for example, radiation therapy. The radiation used in radiation therapy can be ionizing radiation. Radiation therapy can also be gamma rays, X-rays, or proton beams. Examples of radiation therapy include, but are not limited to, external-beam radiation therapy, interstitial implantation of radioisotopes (I-125, palladium, iridium), radioisotopes such as strontium-89, thoracic radiation therapy, intraperitoneal P-32 radiation therapy, and/or total abdominal and pelvic radiation therapy. For a general overview of radiation therapy, see Hellman, Chapter 16: Principles of Cancer Management: Radiation Therapy, 6th edition, 2001, DeVita et al., eds., J. B. Lippencott Company, Philadelphia. The radiation therapy can be administered as external beam radiation or teletherapy wherein the radiation is directed from a remote source. The radiation treatment can also be administered as internal therapy or brachytherapy wherein a radioactive source is placed inside the body close to cancer cells or a tumor mass. Also encompassed is the use of photodynamic therapy comprising the administration of photosensitizers, such as hematoporphyrin and its derivatives, Vertoporfin (BPD-MA), phthalocyanine, photosensitizer Pc4, demethoxy-hypocrellin A; and 2BA-2-DMHA.

In various embodiments, therapies include, for example, immunotherapy. Immunotherapy may comprise, for example, use of cancer vaccines and/or sensitized antigen presenting cells. The immunotherapy can involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). Immunotherapy can also focus on using the cytotoxic lymphocyte-recognized epitopes of cancer cell lines.

In various embodiments, therapies include, for example, hormonal therapy, Hormonal therapeutic treatments can comprise, for example, hormonal agonists, hormonal antagonists (e.g., flutamide, bicalutamide, tamoxifen, raloxifene, leuprolide acetate (LUPRON), LH-RH antagonists), inhibitors of hormone biosynthesis and processing, and steroids (e.g., dexamethasone, retinoids, deltoids, betamethasone, cortisol, cortisone, prednisone, dehydrotestosterone, glucocorticoids, mineralocorticoids, estrogen, testosterone, progestins), vitamin A derivatives (e.g., all-trans retinoic acid (ATRA)); vitamin D3 analogs; antigestagens (e.g., mifepristone, onapristone), or antiandrogens (e.g., cyproterone acetate).

The duration and/or dose of treatment with anti-cancer therapies may vary according to the particular anti-cancer agent or combination thereof. An appropriate treatment time for a particular cancer therapeutic agent will be appreciated by the skilled artisan. The invention contemplates the continued assessment of optimal treatment schedules for each cancer therapeutic agent, where the genetic signature of the cancer of the subject as determined by the methods of the invention is a factor in determining optimal treatment doses and schedules.

In various embodiments, the subject for whom predicted efficacy of an anti-cancer therapy is determined, is a mammal (e.g., mouse, rat, primate, non-human mammal, domestic animal such as dog, cat, cow, horse), and is preferably a human. In another embodiment of the methods of the invention, the subject has not undergone chemotherapy or radiation therapy. In alternative embodiments, the subject has undergone chemotherapy or radiation therapy. In related embodiments, the subject has not been exposed to levels of radiation or chemotoxic agents above those encountered generally or on average by the subjects of a species. In certain embodiments, the subject has had surgery to remove cancerous or precancerous tissue. In other embodiments, the cancerous tissue has not been removed, e.g., the cancerous tissue may be located in an inoperable region of the body, such as in a tissue that is essential for life, or in a region where a surgical procedure would cause considerable risk of harm to the patient, or e.g., the subject is given the anticancer therapy prior to removal of the cancerous tissue.

EXAMPLES

The following examples are not intended to limit the scope of the claims to the invention, but are rather intended to be exemplary of certain embodiments. Any variations in the exemplified methods which occur to the skilled artisan are intended to fall within the scope of the present invention.

Analysis of single mRNAs by PCR suggests that the presence of quantifiable tumor RNA in plasma may allow the development of non-invasive diagnostic and prognostic tools. Extracellular RNA (exRNA) in body fluids is protected from RNAses by RNA binding proteins and extracellular vesicles (EVs). EVs are membrane-enclosed particles that are shed by all cell types in unicellular and multicellular organisms during normal and pathological states, including cancer. EVs play an important role in intercellular communication. Increasing in vitro and in vivo evidence indicates that they act through specific mechanisms involving the transfer of oncogenic molecules between cell and tissue compartments, including at metastatic sites. It is increasingly clear that cancer cells can shed heterogeneous populations of EVs, which differ in size, molecular cargo, function, and likely in biogenesis. The term "EVs" includes 30-150 nm exosomes (Exo), as well as larger particles, frequently described as microvesicles or ectosomes (up to 1 mm diameter). A new category of atypically large EVs (1-10 mm), referred to as large oncosomes (LO), results from the shedding of non-apoptotic membrane blebs produced by highly migratory and metastatic "amoeboid" cancer cells. LO are associated with advanced prostate cancer in vivo and can also be produced by cancer cells of different organ types in association with invasive behavior and other aggressive characteristics. Recent studies suggest that diverse classes of EVs might contain different RNA profiles, as demonstrated by electropherogram.

Molecules carried in EVs are functional and can potentially be used as clinical biomarkers. EV RNA appears particularly promising with respect to the potential of developing minimally invasive tests with high sensitivity and specificity. RNA types identified in EVs include miRNA (often reported as the most abundant RNA species in EVs), ribosomal RNA (rRNA), transfer RNA (tRNA), long non-coding RNA (lncRNA), piwi-interacting RNA (piRNA), small nuclear RNA and small nucleolar RNA (snoRNA). Messenger RNA (mRNA) has also been identified in EVs from cancer cells as a functional regulator of target cell behaviour, and functional transfer of RNA has been displayed in mice using a Cre recombinase system for in vivo identification of tumour cells that take up EVs.

Patterns of mRNA enrichment in EVs can vary significantly across cell types and populations. For example, mRNAs involved in cell migration, angiogenesis, and cell proliferation have been identified in glioblastoma cell-derived EVs, whereas mouse mast cells (MC/9) contain mRNAs responsible for protein synthesis, RNA post-transcriptional modification and cellular development. Despite some evidence suggesting the possibility of a common sequence in the 3'-UTR of mRNAs enriched in EVs, the exact mechanism for selective packaging of mRNA in EVs remains unknown. Previous studies on comparative miRNA profiling in EVs and donor cells suggest that miRNA secretion is an active, ATP-dependent process, and that specific types of miRNA are exported in EVs. Conversely, data showing that extracellular miRNA levels mirror their intracellular abundances favor the hypothesis that miRNA export is a non-selective process. So far, RNA profiling in EVs has been commonly performed by qRT-PCR analysis of single RNAs, rather than by large-scale profiling, an approach that relies on previously discovered RNAs. RNA-Seq has only been employed in a few studies to characterize EV RNA. However, because of a reported predominance of short non-coding RNA in EVs, these RNA-Seq studies have been conducted using small RNA libraries that by design exclude long mRNA.

In the present study, we employed exome capture-based RNA-Seq to profile the mRNA in two types of EVs, Exo and LO, and to determine whether the observed differences between EVs and originating glioblastoma cells might inform the derivation of EVs from a particular subcellular compartment. We examined differences in the mRNA splicing state, level of enrichment of mRNAs encoding a signal peptide, and the content of short half-life mRNAs between the EVs and cells. We extended the analysis to an ENCODE collection of whole-cell, cytosolic, and nuclear mRNA fractions obtained from diverse cancer cell lines in order to derive more general information on the subcellular derivation of the mRNA exported in EVs. Finally, we analyzed the whole transcriptome of EVs purified from the plasma of 10 patients with breast cancer and 5 control individuals to test the potential value of circulating EVs as carriers of tumour-derived RNA.

Experimental Methods
  Cell Culture.
  U87 cells were cultured, as previously described (Morello M. et al. Large oncosomes mediate intercellular transfer of functional microRNA. Cell Cycle 2013; 12:3526-36), in MEM medium supplemented with 10% fetal bovine serum 2 mmol/L L-glutamine, 100 U/ml penicillin, and 100 µg/ml streptomycin. Unless otherwise specified, media and supplements were from Invitrogen.

Purification of EVs.
  The cells were cultured in serum free media for 24 hours prior to EV purification. EVs were then purified from conditioned medium by differential centrifugation as previously described (Minciacchi V R, et al. Large oncosomes contain distinct protein cargo and represent a separate functional class of tumor-derived extracellular vesicles. Oncotarget 2015; 6:11327-41; Di Vizio D, et al. Large oncosomes in human prostate cancer tissues and in the circulation of mice with metastatic disease. Am J Pathol 2012; 181:1573-84; Morello M, et al. Large oncosomes mediate intercellular transfer of functional microRNA. Cell Cycle 2013; 12:3526-36). Briefly, cells and debris were eliminated by centrifugation at 2,800 g for 10 min. The supernatant was then centrifuged using a Beckman SW28 rotor at 10,000 g for 30 min to precipitate large EVs. The remaining supernatant was subjected to additional centrifugation at 100,000 g for 60 min for nano-sized EV isolation. Both the 10,000 g and 100,000 g pellets were collected in TRIzol reagent (Invitrogen) for RNA isolation.

EV Isolation from Plasma.
  Plasma samples from breast cancer patients (n=10) and healthy donors (n=5) were obtained through an Institutional Review Board approved protocol at Cedars-Sinai Medical Center in compliance with the Declaration of Helsinki. All subjects provided written informed consent for blood to be used for research purposes. EVs were isolated from 1 ml of plasma per patient by differential centrifugation. The pellets containing large and small EVs were collected in TRIzol reagent (Invitrogen) and combined for RNA isolation.

RNA Isolation and Profiling.
  Total RNA was extracted from U87 cells and derived large oncosome (LO) and nano-sized EV (Exo) fractions, as well as from plasma EVs by ethanol precipitation. RNA was quantified using NanoDrop2000 and the RNA yield was normalized over the total protein amount (ng). The quality of RNA was assessed by total RNA electropherogram profile, using an Agilent 2100 bioanalyzer (Total RNA Nano Series II).

Western Blot.
  Protein lysates from U87 whole cells, LO and Exo were blotted with: rabbit monoclonal HSPA5 (C50B12) (Cell Signaling), GM130 (Cell Signaling), and mouse monoclonal CD81 (M38) (Abcam), at 1:1000 dilution, and HRP conjugated GAPDH (14C10) (Cell Signaling), at 1:2000 dilution.

Library Preparation for Next-Generation Sequencing.
  Approximately 200 ng of total RNA from U87 cells, LO and Exo, and 1 to 10 ng of total RNA from the circulating EV samples were used for the preparation of paired-end libraries. These libraries were made using a pre-release version of the Illumina RNA Access kit (http://www.illumina.com/products/truseq-rna-access-kit.html). Briefly, this protocol uses random priming to create $1^{st}$ and $2^{nd}$ strand cDNA from total RNA. No poly-A selection or rRNA depletion is done prior to creation of cDNA. The total cDNA libraries are then enriched for protein coding regions of mRNA by hybridization and capture using a set of probes designed against 21,415 human genes. Each library was analyzed on one lane of an Illumina GAIIx instrument. RNA-Seq reads were then aligned to the human genome.

RNA-Seq Validation by RT-qPCR.
  We used high-throughput on chip quantitative RT-PCR using a 48×48 dynamic array (Fluidigm Corporation) (Mitra A K, et al. Single-cell analysis of targeted transcriptome predicts drug sensitivity of single cells within human myeloma tumors. Leukemia 2015). The assay plate contained specific primers for AARS, KLF2, RIN1, ADRBK1, MMP14, RRM2, ASL, MTRNR2L2, SLC7A5, DAZAP1, MTRNR2L9, TK1, E2F1, P4HB, TMEM41B, HBA1, PHF19, TPM1, HBA2, POMP, TSNARE1, HSPA5, PSAP and ZNF789 (id: 5578_FDGP_15). Primer sequences and amplicon length are shown in Table 2. cDNA was obtained from 11 ng of input RNA from U87 cells, LO and Exo using the Fluidigm Reverse Transcription Master Mix. Additional PCR experiments included quantitative detection of VEGFA (5'-CTTGCCTTGCTGCTCTACC-3' (SEQ ID NO: 1) forward and 5'-CACACAGGATGGCTTGAAG-3' (SEQ ID NO: 2) reverse) in endothelial cells exposed to U87-derived LO.

Immunofluorescent (IF) Imaging.

The lentiviral pCSII-EF-DHB-YFP vector was kindly provided by Dr. Sabrina Spencer, University of Colorado. U87 cells stably expressing DHB-YFP were made using lentiviral pCSII-EF-DHB-YFP vector as previously described (Spencer S L, et al. The proliferation-quiescence decision is controlled by a bifurcation in CDK2 activity at mitotic exit. Cell 2013; 155:36983). IF staining of membrane with DiI was performed according to the manufacturer's protocol (Life Technologies, Grand Island, N.Y.). Stained cells were fixed in 4% paraformaldehyde (PFA), and coverslips were mounted in Vectashield mounting medium containing DAPI (4',6'-diamido-2-phenylindole) (Vector Laboratories, Burlingame, Calif.). Images were taken using Leica SP5-X confocal fluorescent microscopy.

RNA can be Extracted from Both Large Oncosomes and Exosomes

Figure 1B:
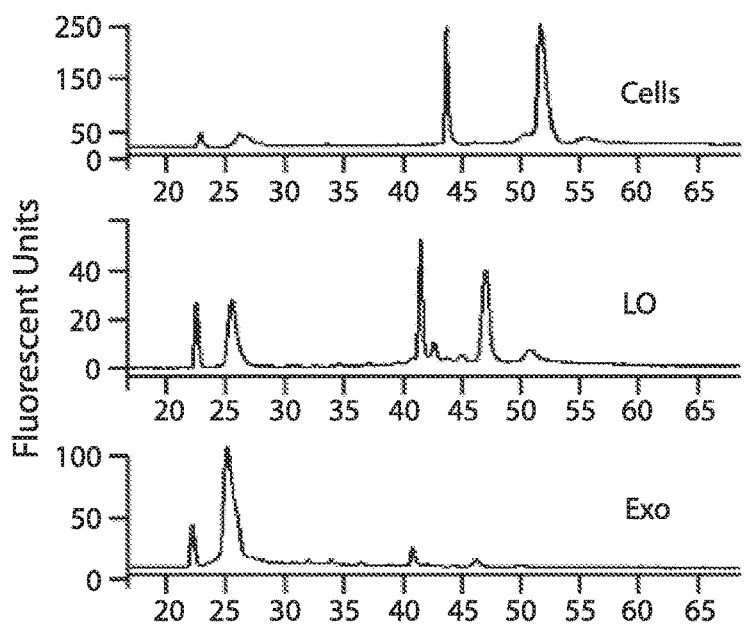
Figure 1C:
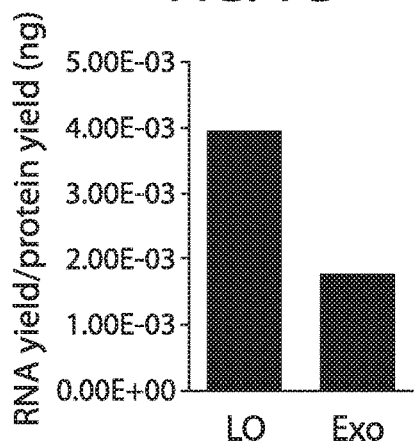
Figure 1D:
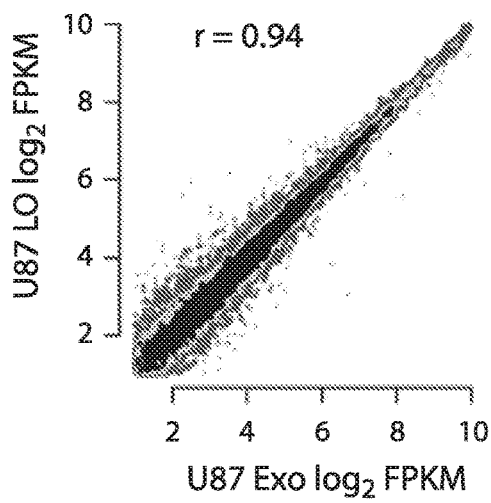

LO and Exo were isolated from the conditioned medium of glioblastoma U87 cells by a differential centrifugation-based protocol that can differentiate LO from Exo, as confirmed by flotation in iodixanol. Western blotting with GAPDH and HSPA5, which are enriched in LO, CD81, which is typically enriched in Exo, and the Golgi protein GM130, which is typically excluded from EVs, confirmed the purity of our preparations (FIG. 1A). Analysis of the RNA quality by electropherogram demonstrated that 18S and 28S rRNA peaks and longer RNA species (up to 4,000 bp) were well recognizable in the LO preparations while undetectable in Exo (FIG. 1B). Along with this qualitative difference in RNA profiles, RNA yields, normalized to the number of originating cells and total protein amount, was also higher in LO (2.2 fold) than in Exo (FIG. 1C).

Extravesicular mRNA Reflects the Profile of the Originating Tumour Cells

In order to determine whether the mRNA content of the EVs reflects the mRNA of the originating tumour cells, we isolated and sequenced mRNA populations from U87 cells and from derived LO and Exo. We obtained a minimum of 50 million paired end reads over 2 million uniquely mapped reads in Exo, and over 5 million uniquely mapped reads in LO (Table 1).

TABLE 1

Sizes of read sets in U87 RNA-Seq data and mapping rates

| Set | Read Pairs | Non-duplicate pairs | Pairs mapped (%) |
|---|---|---|---|
| U87 Exo | 59,015,762 | 2,282,205 | 94% |
| U87 LO | 12,045,233 | 5,003,737 | 93% |
| U87 Cells | 133,434,652 | 29,870,442 | 97% |

Approximately 200 ng of total RNA from U87 cells, LO and Exo, and 1 to 10 ng of total RNA from the circulating EV samples were used for the preparation of paired-end libraries. These libraries were made using a pre-release version of the Illumina RNA Access kit (www.illumina.com/products/truseq-rna-access-kit.html). Briefly, this protocol uses random priming to create $1^{st}$ and $2^{nd}$ strand cDNA from total RNA. No poly-A selection or rRNA depletion is done prior to creation of cDNA. The total cDNA libraries are then enriched for protein coding regions of mRNA by hybridization and capture using a set of probes designed against 21,415 human genes. Each library was analyzed on one lane of an Illumina GAIIx instrument. RNA-Seq reads were then aligned to the human genome.

TABLE 2

Primer Sequences for validated genes.
The amplicon length varies
between 64 and 136 bp (average 98 bp)

| Target gene | Forward | Reverse | Amplicon bp |
|---|---|---|---|
| AARS | ACAATGAGGCTGGCA AGATCA (SEQ ID NO: 3) | ACCCACTCGCTGGCT TTTAA (SEQ ID NO: 4) | 82 |
| ADRBK1 | TGCAGAAGTACCTGG AGGAC (SEQ ID NO: 5) | GAAGTCTCGGAAGAG CAGGTA (SEQ ID NO: 6) | 86 |
| ASL | GGGCCATTGCAGGCA ATCC (SEQ ID NO: 7) | TGTTGAGAGTGATGG CCCCAAA (SEQ ID NO: 8) | 81 |
| DAZAP1 | GATCTATGACGCCGA GAAGCA (SEQ ID NO: 9) | CCACTGATTGTTCGT CCTCGAA (SEQ ID NO: 10) | 71 |
| E2F1 | AGCTCATTGCCAAGA AGTCCAA (SEQ ID NO: 11) | TCCTGGGTCAACCCC TCAA (SEQ ID NO: 12) | 94 |
| HBA1 | TCTCCTGCCGACAAG ACCAA (SEQ ID NO: 13) | GTGGTGGGGAAGGAC AGGA (SEQ ID NO: 14) | 110 |
| HBA2 | CCACTGCCTGCTGGT GAC (SEQ ID NO: 15) | TACCGAGGCTCCAGC TTAAC (SEQ ID NO: 16) | 136 |
| HSPA5 | CGCTGAGGCTTATTT GGGAA (SEQ ID NO: 17) | TTGGCGTTGGGCATC ATTAA (SEQ ID NO: 18) | 79 |
| KLF2 | ATCCTGCCGTCCTTC TCCA (SEQ ID NO: 19) | CCATGGACAGGATGA AGTCC (SEQ ID NO: 20) | 136 |
| MMP14 | GTAACAGGCAAAGCT GATGCA (SEQ ID NO: 21) | AGCCCCAAACTTGTC TGGAA (SEQ ID NO: 22) | 78 |
| MTRNR2L2 | ACCCATTCCACCTTA CTACCA (SEQ ID NO: 23) | TCTATTGCGCCGGTT TACAA (SEQ ID NO: 24) | 90 |
| MTRNR2L9 | CTAACCGTGCAAAGG TAGCA (SEQ ID NO: 25) | GGTCAGTTGCAGTGG TTGAA (SEQ ID NO: 26) | 106 |
| P4HB | CAACAGTGACGTGTT CTCCAA (SEQ ID NO: 27) | CAAAGTTGTTCCGGC CTTCA (SEQ ID NO: 28) | 86 |

TABLE 2-continued

Primer Sequences for validated genes.
The amplicon length varies
between 64 and 136 bp (average 98 bp)

| Target gene | Forward | Reverse | Amplicon bp |
|---|---|---|---|
| PHF19 | TTCTGCTCCGTGTGT AACCA (SEQ ID NO: 29) | ATTATAGAGGGCCAG GTGAACC (SEQ ID NO: 30) | 87 |
| POMP | TCAGCAAGTGGACCT TTTGAA (SEQ ID NO: 31) | CAAGGGGATGACTAG GCAAAA (SEQ ID NO: 32) | 88 |
| PSAP | ATCCTGGCTGCTCTT GAGAAA (SEQ ID NO: 33) | GCTCGTACTCTGCCA CAAAC (SEQ ID NO: 34) | 85 |
| RIN1 | AGAAGCTGCTGTCGC CTAA (SEQ ID NO: 35) | CTTGAGCACAGAGCA ATGCA (SEQ ID NO: 36) | 68 |
| RRM2 | GCAGCAAGCGATGGC ATA (SEQ ID NO: 37) | GAAACAGCGGGCTTC TGTAA (SEQ ID NO: 38) | 81 |
| SLC7A5 | TTCGGGGTCTGGTGG AAAA (SEQ ID NO: 39) | CCTGCATGAGCTTCT GACAC (SEQ ID NO: 40) | 85 |
| TK1 | GGGCCGATGTTCTCA GGAA (SEQ ID NO: 41) | CTTGATCACCAGGCA CTTGTAC (SEQ ID NO: 42) | 87 |
| TMEM41B | GATCAGCAAGAATGT CACTCC (SEQ ID NO: 43) | TCTCTGGGAACCTTC ATATTCAC (SEQ ID NO: 44) | 130 |
| TPM1 | GGTCCTTTCCGACAA GCTGAA (SEQ ID NO: 45) | AGTTACTGACCTCTC CGCAAAC (SEQ ID NO: 46) | 64 |
| TSNARE1 | TCAAGGACTTGGCCT CCA (SEQ ID NO: 47) | CCTCAAGGCTGGCTT CAATA (SEQ ID NO: 48) | 69 |
| ZNF789 | GCGGCTTGGCGGAGA TT (SEQ ID NO: 49) | TTCCACGGCCTGGTC TTTTG (SEQ ID NO: 50) | 83 |

Extravesicular mRNA is Derived from Cytosolic mRNA

Figure 1E:
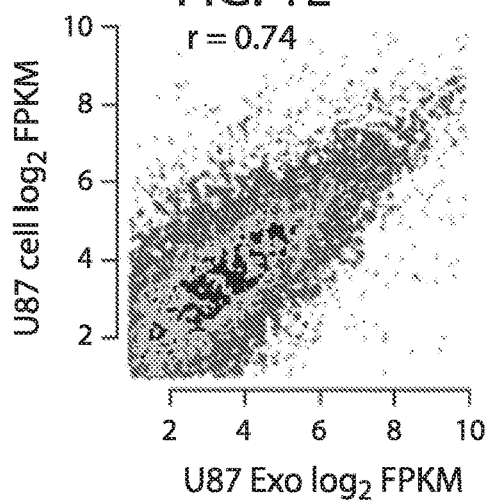
Figure 1F:
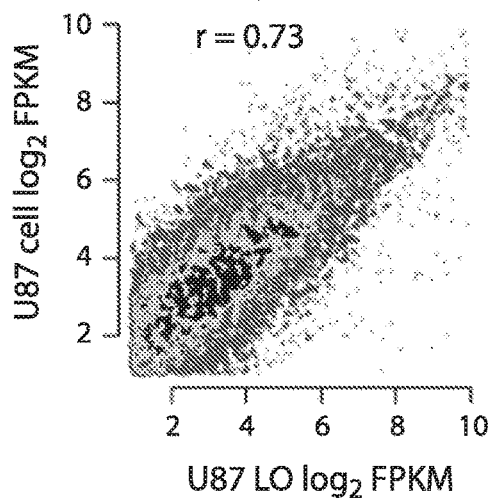
Figure 1G:
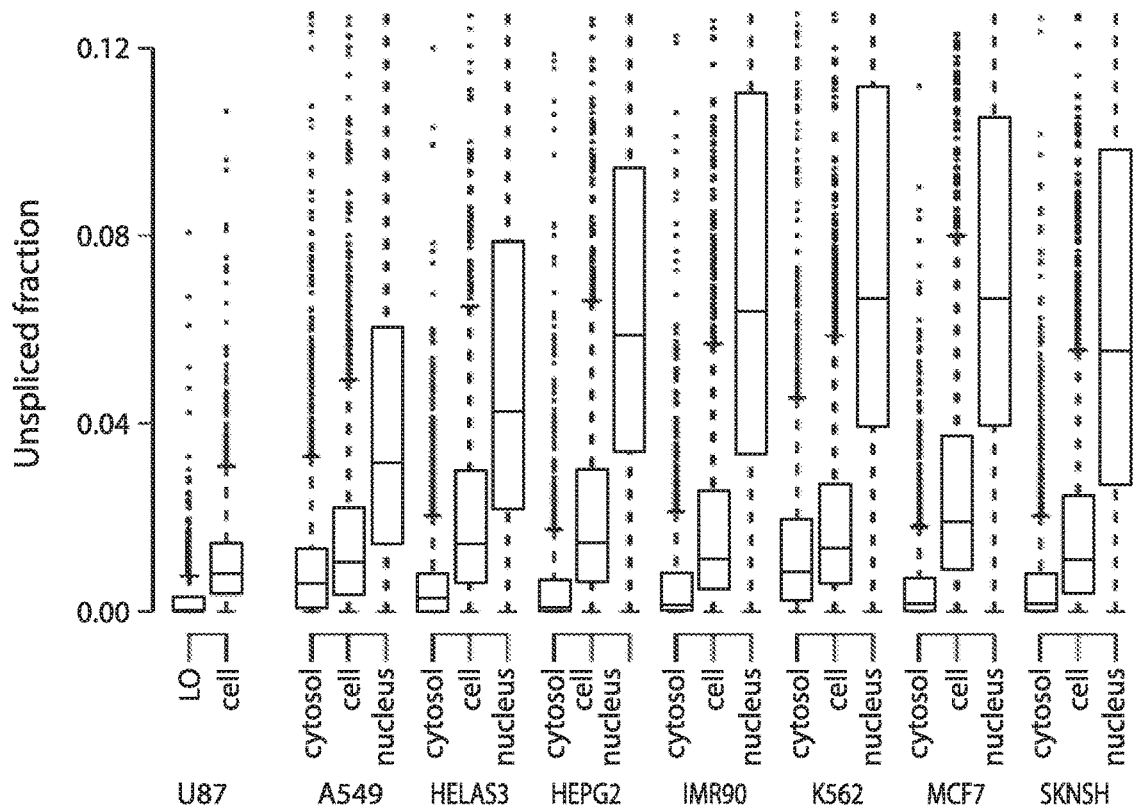

We hypothesized that the observed differences between EV and whole-cell mRNA profiles are potentially due to the EVs being derived from specific cellular or subcellular compartments. To test this hypothesis, we queried the Cold Spring Harbor RNA-Seq dataset of the ENCODE project, including various cancer cell lines and multiple subcellular compartments. We first observed similar differences between the mRNA populations of whole cell and cytosol (r=0.79-0.91) (FIG. 5) to those observed between the U87 EVs and cells (r=0.73-0.74) (FIG. 1E, FIG. 1F). Next, to assess the origin of EV mRNA from cytosolic versus non-cytosolic cell compartments, we focused on the unspliced mRNA, i.e. intronic sequence, that is known to be comparatively less abundant in cytoplasm than in either whole-cell or nuclear compartments. We characterized the presence of unspliced mRNA in U87 cells and LO and compared our RNA-Seq data to cancer cell line data from the ENCODE project (FIG. 1G) that included cytosolic, whole-cell, and nuclear mRNA fractions. We found that the LO fraction contains significantly less unspliced mRNA (p≈0, Wilcoxon rank-sum) than the originating U87 cells. U87 Exo were not included in the analysis due to substantially fewer non-redundant reads in the dataset. A similar difference was seen within the ENCODE cell lines, with the cytosolic fractions having significantly less unspliced mRNA than the corresponding whole-cell fractions, which in turn had less unspliced mRNA than the nuclear fractions. The similar pattern seen when comparing splicing between LO and whole-cell mRNA, and between cytosol and whole-cell mRNA, is suggestive of a cytosolic origin for the EV mRNA.

Figure 1H:
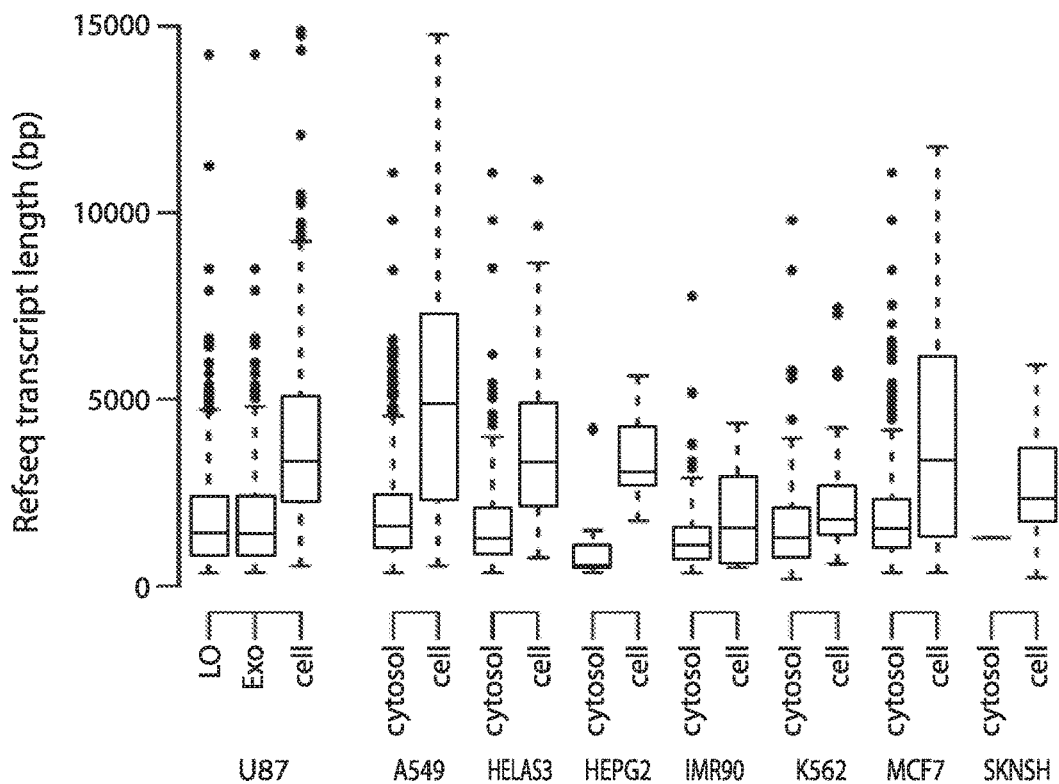

To investigate this further, we then compared the annotated transcript length of mRNAs enriched (>3-fold higher) or depleted (>3-fold lower) in U87 EVs compared to whole cells in our dataset, and in the cytosol of ENCODE cell lines compared to whole cells (FIG. 1H). This comparison showed that transcripts enriched in either U87 EV fraction tend to be significantly shorter than those enriched in the U87 cells (p≈0 for Exo, p≈0 for LO, Wilcoxon), with a similar result for the cytosol of most ENCODE cell lines, further corroborating a cytosolic origin of EVs. Lastly, as new mRNAs are not generated in the cytosol, but rather in the nucleus, it would be expected that short half-life mRNAs, which are degraded faster, would be depleted from the cytosol when compared to the whole cell. Using annotated mRNA half-life data from a published study, we compared fold changes in mRNA abundance both between U87 EV sets and whole cells, and ENCODE data from cytosol and whole cell, grouping fold-changes by long and short mRNA half-life. For both the Exo and LO data, and the majority of ENCODE cell lines, shorter half-life mRNAs showed lower fold-changes than long half-life mRNAs ($p=8.2e^{-5}$ for Exo, $p=2.7e^{-7}$ for LO, Wilcoxon), further arguing for a cytosolic origin of the mRNA cargo in EVs.

Signal Peptide Bearing mRNAs are Depleted from EVs

Figure 2A:
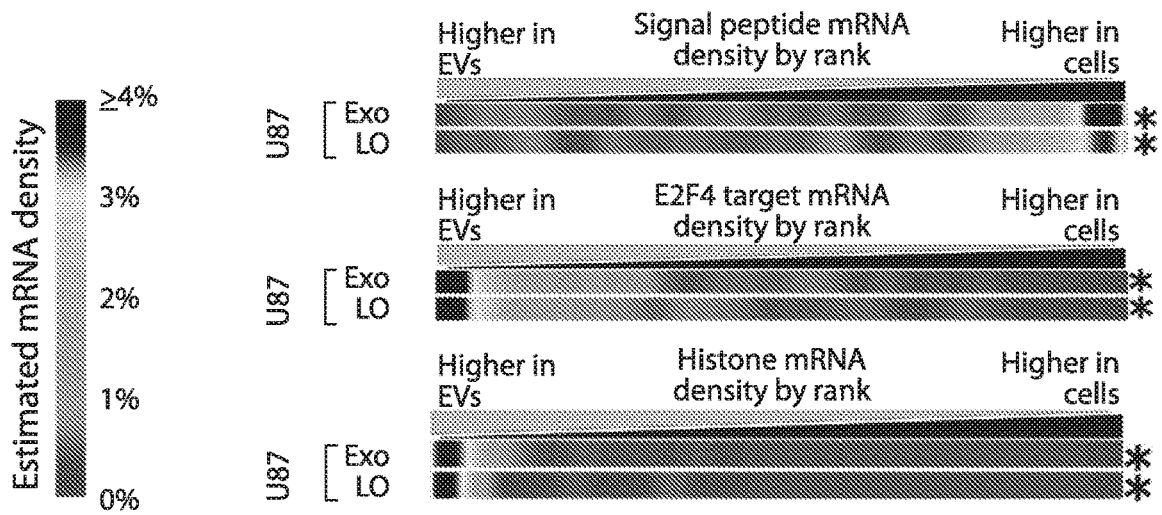
FIG. 2A-FIG. 2C depict in accordance with various embodiments of the invention, that U87 EVs are derived from U87 cytosol and enriched for S-phase associated transcripts.

The mRNA population of the cytosol is not uniformly distributed, particularly with regard to mRNAs encoding a signal peptide. Many eukaryotic genes encode an N-terminal signal peptide that is recognized by the Signal Recognition Particle and directs the mRNA to the rough endoplasmic reticulum (RER) for translation. mRNAs encoding a signal peptide are more likely to be associated with the RER than free in the cytosol. Based on this notion, if the RER were involved in the generation of EVs it would be expected that mRNAs encoding a signal peptide would be enriched in EVs compared to cells. Signal peptides can be accurately predicted computationally via machine learning using the SignalP utility. We therefore used SignalP to assess all protein coding genes in the human genome for the presence of a signal peptide; we then compared the abundance of signal peptide encoding mRNAs between U87 EVs and cells, and between ENCODE cytosol and whole-cell (FIG. 2A). We found that EVs were strongly depleted for signal peptide-encoded mRNAs (p<0.001, NES=−3.1, GSEA, mean log 2 fold-change=−1.0.). The signal peptide depletion was not observed when we compared cytosol and whole cells in the ENCODE dataset. The depletion of signal peptide-bearing mRNAs from the EVs suggests that EVs are formed to the exclusion of mRNAs co-translationally bound to the RER. Such a depletion of signal peptide encoding mRNAs also argues strongly for a cytosolic origin of the mRNA in the EVs, since signal peptide recognition is itself a cytosolic process.

U87 EVs are Enriched in S-Phase Specific Transcripts

We found that several important cell cycle regulators were enriched in EVs, including E2F (~40-fold) and CDK2 (~7-fold), suggesting a possible relationship between progression through the G1-S checkpoint and mRNA export.

New mRNA is unlikely to be generated in the EVs; rather, the mRNA content of EVs likely reflects the mRNA state of the cytosol at the time of EV biogenesis. Depletion or enrichment of mRNA that is expressed during a specific phase of the cell cycle permits inference of a phase-specific origin of EV mRNA. Notably, CDK2 is involved in the transition to the S-phase of the cell cycle via phosphorylation of the Rb family members and the concomitant release of E2F transcription factors. The E2F family of transcription factors is responsible for both repressing and enhancing the cell cycle-specific expression of many genes, with targets tending to have peak expression in late G1 and S-phase. Indeed, the E2F1 gene itself is known to peak during G1 and S-phases. Comparing EV and whole cell profiles, we found that mRNAs of genes with E2F binding motifs near or in their promoters are significantly enriched in EVs ($p<0.001$, NES=2.5). This enrichment is not seen when comparing cytosol and whole-cell RNA-Seq data in ENCODE cell lines, indicating that it is not due to the cytosolic origin of the EV mRNA. CDC2/CDK1 is a heavily E2F regulated gene; release of the repressive of E2F4, a paralog of E2F1 with a common DNA binding motif and highly overlapping target gene set, from the CDC2 promoter region precedes the transcriptional activation of CDC2. In our RNA-Seq data, we found that CDC2/CDK1 is increased >100-fold in EVs compared to cells. To examine genome-wide the differences in E2F family targets between U87 EVs and cells, we defined a set of E2F regulated genes using ENCODE ChIP-seq data for the broadly expressed E2F4 protein. Comparing the abundance of mRNAs from this gene set between EVs and cells we found that the EV sets are greatly enriched for these mRNAs, (p 0.001, NES=3.6, mean log 2fold-change=1.1) (FIG. 2A), suggesting that most mRNAs are exported in EVs at a time in the cell cycle when E2F4 targets are de-repressed, most likely in the G1 or S-phases. Enrichment of this E2F4 regulated gene set was not observed when comparing the cytosol to whole cell of any of the ENCODE cell lines. The expression of canonical human histone genes is similarly regulated by the cell cycle, being largely confined to the S-phase, followed by their degradation in G2. As with the E2F targets, we found that these histone mRNAs are enriched in EVs ($p \leq 0.001$, NES=3.37, mean log 2 fold-change 2.5, FIG. 2A). The histone mRNAs were also slightly enriched in the cytosol from several ENCODE cell lines (NES=−1.2-2.9). However, compared to the EVs, the fold-change of histone mRNAs in the cytosolic datasets was significantly lower (mean log 2 fold change 0.4-1.53), suggesting that the enrichment in EVs cannot be solely explained by cytosolic localization of histone mRNAs. The enrichment of histone mRNAs in the EVs, combined with the similar strong enrichment of E2F targets, suggests that most of the mRNA is exported to EVs during the S-phase of the cell cycle, when both gene sets are highly expressed. The implication of this result is that profiling EV mRNA could capture a snapshot of cytosolic, S-phase mRNA.

Patterns Seen in U87 RNA-Seq Data are Recapitulated in Expression Microarrays

Figure 2B:
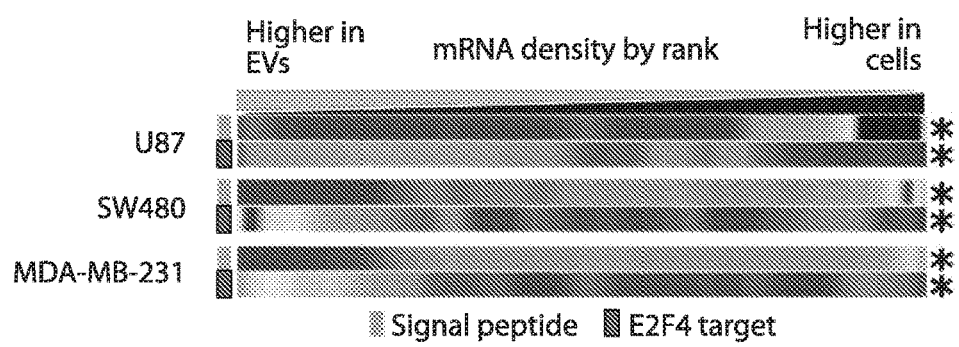

Using expression microarray data from previous studies that have characterized the mRNA content of EVs and originating cells, we detected a robust depletion of signal peptide encoding mRNAs from the EVs of three diverse cancer cell lines, U87 (glioma, $p<0.001$, NES=−2.7, mean fold-change=−1.3), SW480 (colon cancer, $p<0.001$, NES=−2.75, mean log 2 fold-change=−0.3), and MDA-MB-231 (breast cancer, $p<0.001$, NES=−2.6, mean log 2 fold-change=−0.1) (FIG. 2B), in good agreement with observations from our RNA-Seq data. We additionally observed significant enrichment of E2F4 targets in the EVs of all three datasets, U87 ($p<0.001$, NES=1.48, mean log 2 fold-change=0.2), SW480 ($p<0.001$, NES=2.3, mean log 2 fold-change=0.3) and MDA-MB-231 ($p<0.001$, NES=2, mean log 2 fold-change=0.1), again in strong agreement with our U87 RNA-Seq data. Histone genes are not sufficiently spotted on these array platforms for similar analysis. Such concordance across different cell types and expression platforms makes it very unlikely that these patterns are either spurious or are artifacts of library preparation, and the presence of these patterns across diverse cell lines suggests that they may be universal features of EV mRNA.

Increased LO Formation in S-Phase

Figure 2C:
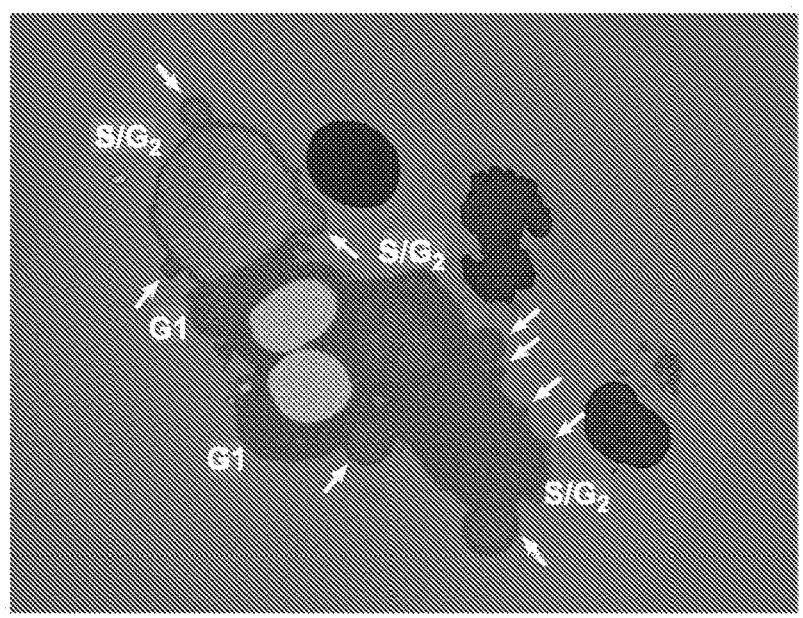

The RNA-Seq and microarray data indicate enrichment for cell cycle relevant mRNAs in EVs. To pursue this finding further, we created stable cell lines expressing the CDK2-responsive portion and nuclear export signal of the DNA helicase B (DHB) gene fused to YFP. The DHB protein is localized in the nucleus during G0 and G1 phases, but translocates to the cytoplasm when phosphorylated by CDK2 at the G1/S transition. YFP-tagging of the CDK2 targeted region of the DHB protein can thus be used as a sensor to track the sub-cellular localization of the protein and, thus, the cell cycle phase of individual cells. Using fluorescent microscopy, we found that LO formation was observed predominantly in the S-phase of the cell cycle (FIG. 2C). A similar result was also observed in breast cancer cells.

Figure 3A:
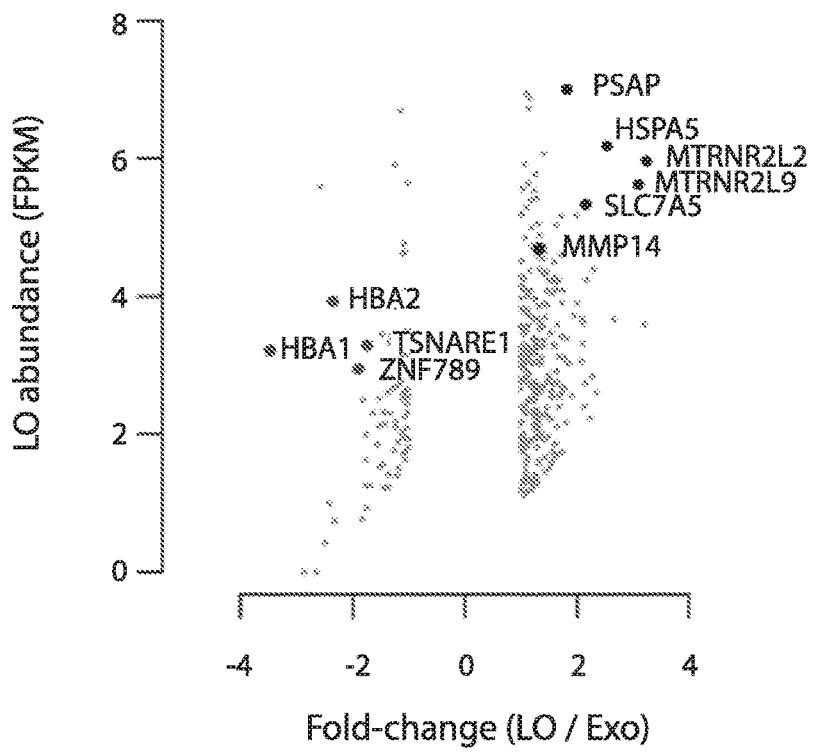
FIG. 3A-FIG. 3F depict in accordance with various embodiments of the invention, that VEGFA appears as one component of biological pathways enriched in LO, and can be transferred to endothelial cells via LO.
Figure 3B:
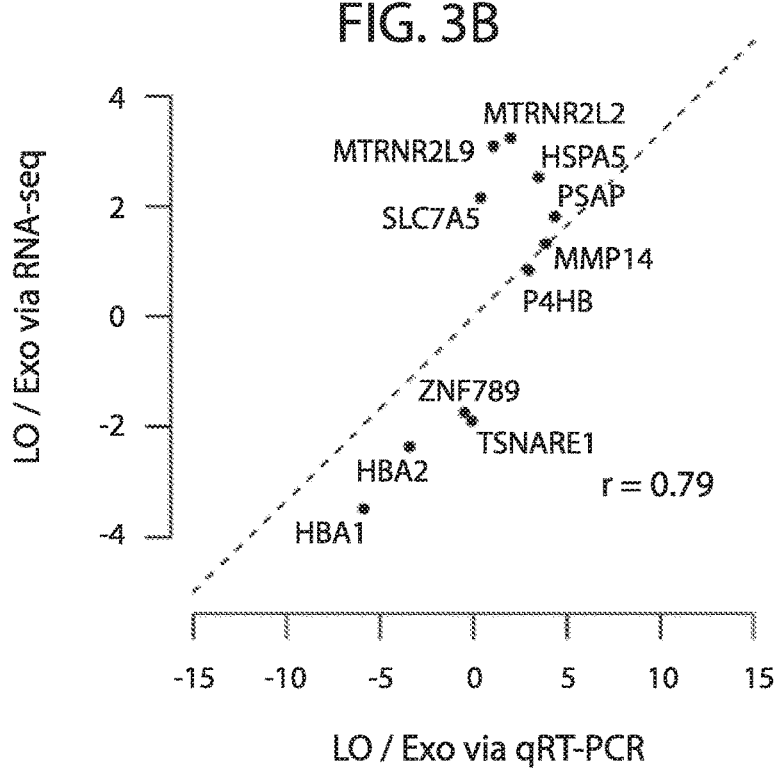

Analysis of Biological Pathways Enriched in LO Versus Exo Leads to Functionally Relevant VEGFA, which can be Transferred to Endothelial Cells Via LO Even though the majority of the transcripts in LO and Exo were present at similar levels in the two sets, 5.2% of transcripts were present at greater than 2-fold difference between LO and Exo (414 enriched and 118 depleted mRNAs in LO in versus Exo) (FIG. 3A). Even when we used the more stringent criteria of at least 5 FPKM for mRNA detectability, 215 mRNAs were enriched and 110 mRNAs were depleted in LO. Ten of 11 (>90%) of these mRNA, which were randomly selected among mRNAs with at least 2 fold differential abundance in LO vs Exo, were validated by a high throughput, microfluidic system. The correlation between RNA-Seq and the microfluidic system data was high (r=0.76) (FIG. 3B, Table 2). HSPA5, which was previously identified as enriched in LO vs Exo at the protein level by mass spectrometry, appeared among the mRNAs that were enriched in LO vs Exo.

Figure 3C:
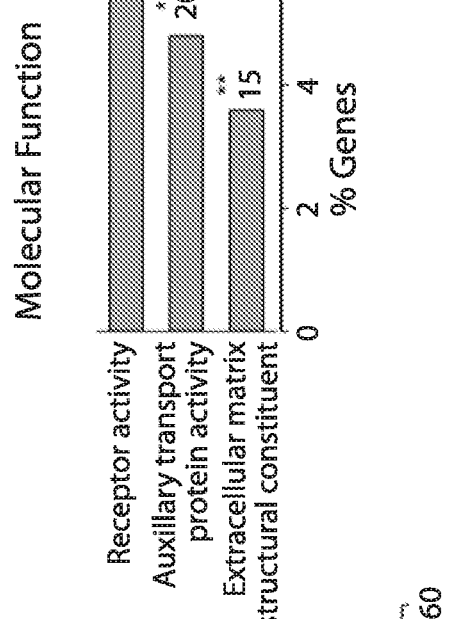
Figure 3D:
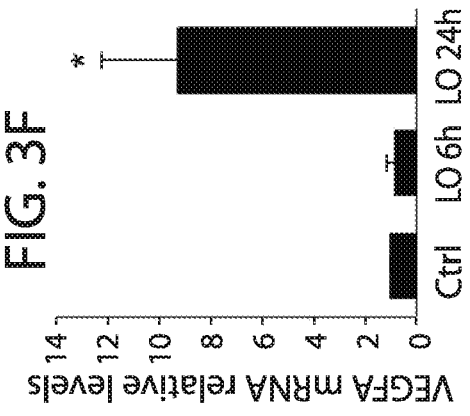
Figure 3E:
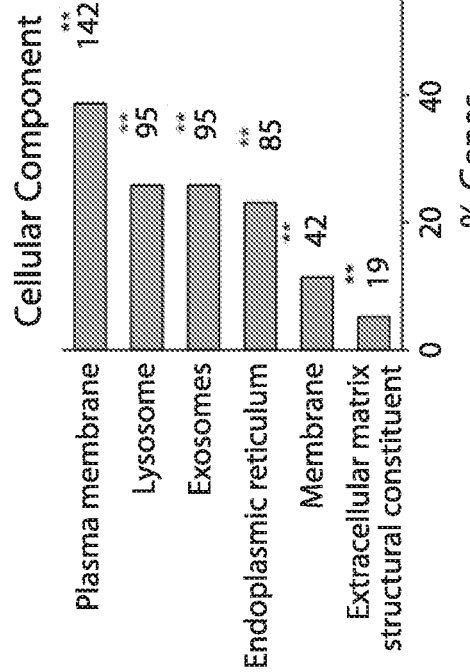
Figure 3F:
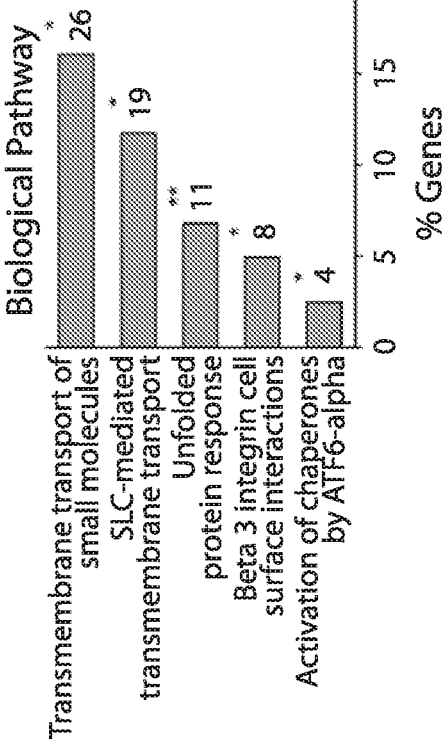

Gene ontology (GO) enrichment analysis using the Fun-Rich tool was performed for all LO-enriched mRNAs. The analysis demonstrated that LO contain high levels of mRNAs that encode proteins localized in membrane structures (FIG. 3C-FIG. 3E). More specifically, the proteins encoded by the mRNAs enriched in LO belong to categories such as plasma membrane (cellular component) and transporters or receptors (molecular function and biological pathway). The biological pathway that caught our attention was the beta3 integrin cell surface interactions group. Recent reports suggest that integrins are enriched in Exo, that beta3 integrin signaling is important in promoting angiogenesis, and that specific integrins can direct cancer metastasis to specific organs. This biological pathway has also been reported to play a role in glioblastoma, and 6 out of 8 components of this pathway have been reported to be significantly enriched in glioblastoma tissue in the Oncomine database. VEGFA, which is a well-known and potent angiogenesis stimulator, belongs to this group and has been shown to be an important mediator of angiogenesis and tumor progression in several human tumor types. Whether this mRNA can be transferred between cells via LO is unknown. Treatment of endothelial cells with LO obtained from U87 cell media for 24 hours resulted in increased VEGFA expression. This was not the case at 6 hour treatment, which is more suggestive of transcriptional induction than RNA transfer (FIG. 3F).

Analysis of 15 Plasma Whole Transcriptomes Identifies a Global EV mRNA Signature and Breast Cancer Signal in Patients Given that our observed signature of differentially abundant mRNA sets between U87 EVs and cells (a depletion of signal peptide encoding mRNAs, and an enrichment of histones and E2F targets) was recapitulated in a range of heterologous cancer cell lines, including breast cancer MDA-MB-231 cells, we used RNA-Seq in an attempt to identify this signature in circulating EVs from the plasma of patients with advanced breast cancer. As a proof of principle, we isolated EVs from the plasma of patients with stage III breast Invasive Lobular Carcinoma (ILC) versus healthy controls (Supplementary Table S3).

TABLE 3

Patient characteristics

| Cancer Category | Histology | Cancer Stage | Tumor Grade | Age diagnosis | ER | PR | HER2 |
|---|---|---|---|---|---|---|---|
| BREAST | Invasive, Lobular (ILC) | IIIA | G2-Moderately differentiated | 49.7 | neg | neg | neg |
| BREAST | Invasive, Lobular (ILC) | IIIB | G2-Moderately differentiated | 46.6 | not known | not known | not known |
| BREAST | Invasive, Ductal (IDC), NOS | IIIA | G3-Poorly or undifferentiate | 43.5 | pos | pos | neg |
| BREAST | Invasive, Ductal (IDC), NOS | IIIA | G2-Moderately differentiated | 39.7 | pos | pos | neg |
| BREAST | Invasive, Ductal (IDC), NOS | IIIA | G3-Poorly or undifferentiate | 34.3 | pos | pos | neg |
| BREAST | Invasive, Ductal (IDC), NOS | III | G2-Moderately differentiated | 50.4 | pos | pos | neg |
| BREAST | Invasive, Ductal (IDC), NOS | III | G2-Moderately differentiated | 91.6 | rare pos | neg | equivocal |
| BREAST | Invasive Micropapillary | III | G3-Poorly or undifferentiate | 56.3 | pos | pos | neg |
| BREAST | Invasive, Lobular (ILC) | III | G2-Moderately differentiated | 62.2 | pos | pos | neg |
| BREAST | Mixed, Ductal/ Lobular | III | G2-Moderately differentiated | 51.0 | pos | pos | neg |

On average, we achieved 26.5 million raw reads (ranging from 5 to 62 million) (Table 4).

TABLE 4

Sizes of read sets in RNA-Seq of human circulating EVs and mapping rates.

| Set | Read pairs | Non-duplicate pairs | Pairs mapped (%) |
|---|---|---|---|
| IDC1 | 8,975,422 | 2,261,267 | 93% |
| IDC2 | 10,126,705 | 412,955 | 94% |
| IDC3 | 30,401,873 | 324,433 | 87% |

TABLE 4-continued

Sizes of read sets in RNA-Seq of human circulating EVs and mapping rates.

| Set | Read pairs | Non-duplicate pairs | Pairs mapped (%) |
|---|---|---|---|
| IDC4 | 21,009,646 | 905,241 | 88% |
| IDC5 | 34,200,494 | 449,574 | 87% |
| ILC/IDC | 5,315,196 | 1,064,974 | 94% |
| ILC1 | 62,483,531 | 1,861,778 | 97% |
| ILC2 | 46,243,982 | 1,949,196 | 95% |
| ILC3 | 25,310,833 | 1,240,972 | 89% |
| IMP | 21,324,751 | 1,009,516 | 87% |
| Normal1 | 19,897,356 | 938,685 | 88% |
| Normal2 | 26,236,895 | 505,776 | 87% |
| Normal3 | 27,986,356 | 535,740 | 82% |
| Normal4 | 21,407,390 | 326,597 | 84% |
| Normal5 | 28,450,598 | 786,680 | 89% |

Figure 4A:
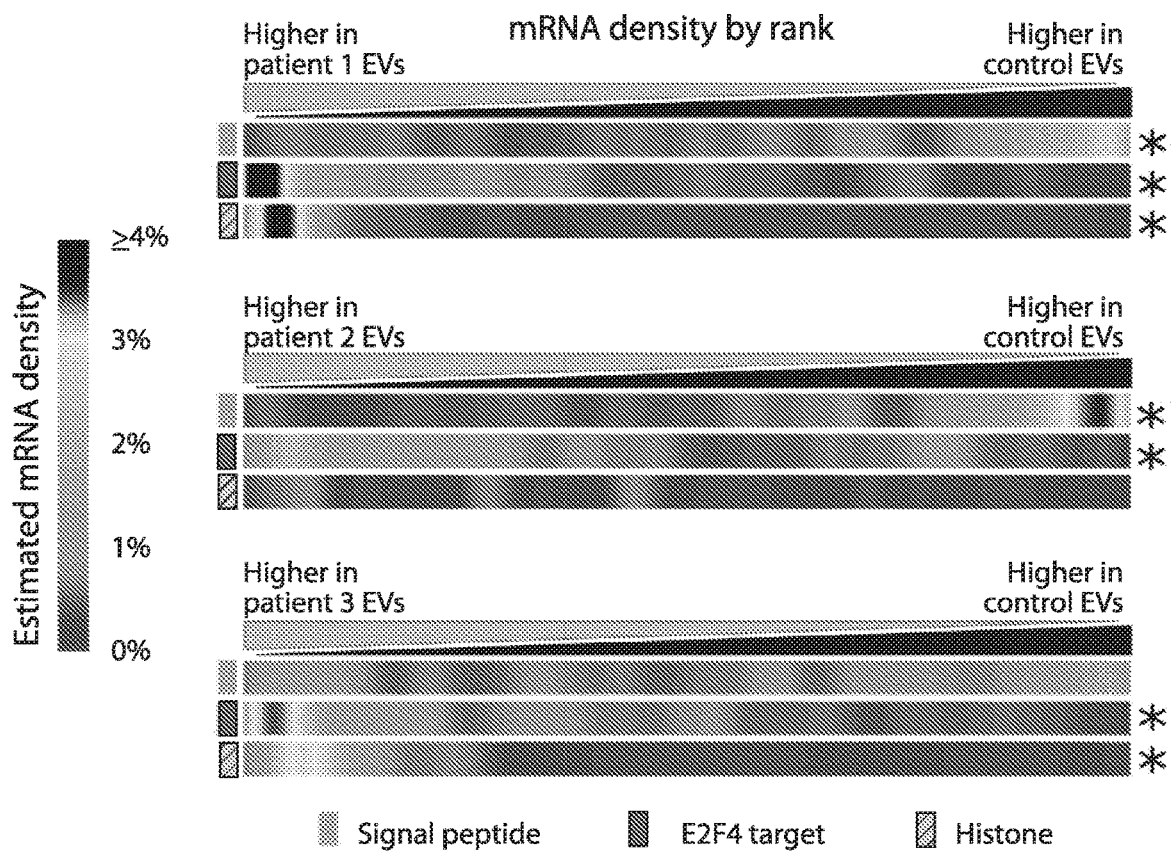
FIG. 4A-FIG. 4C depict in accordance with various embodiments of the invention, that analysis of 15 plasma whole transcriptomes identifies a global EV mRNA signature and breast cancer signal in patients.
Figure 4B:
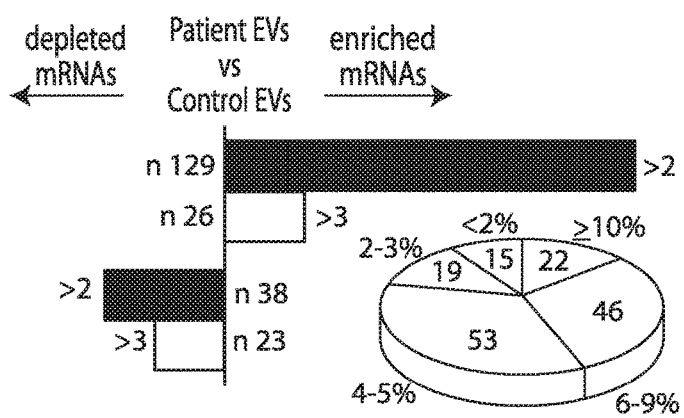
Figure 4C:
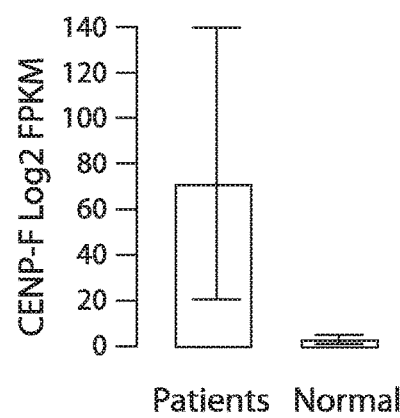

Of these raw reads, 87-97% were uniquely mapped to annotated transcriptional loci. In EV mRNA preparations from patients with ILC, we observed a significant enrichment of E2F4 target genes, and in 2 out of these 3 patients we found enrichment of histone mRNAs and a strong depletion of signal peptide compared to healthy women (FIG. 4A). We then performed RNA-Seq on plasma-derived EVs from an additional group of patients with different histotypes of Stage III breast cancer. 155 mRNAs were enriched and 61 were depleted in the EVs from patient plasma versus healthy controls (FIG. 4B). 145 of the enriched mRNAs were identified in the TCGA database as upregulated (based on z-score) or amplified in patients with breast cancer at different frequency (from 1% to >10%), (FIG. 4B). Additionally, we observed a significant enrichment of GATA1 target genes in plasma EVs from patients compared to healthy women. High GATA1 mRNA levels have been identified in breast cancer tissue. Finally, CENPF was up ~5-fold in plasma EVs from ILC patients versus control women. Notably, a recent seminal study reported increased expression levels of CENPF in 16% of breast cancer tissue samples from patients with ILC. Collectively, these results suggest that an mRNA signature of the disease is visible in the circulating EV mRNA of patients.

TABLE 5

The genes with the highest fold-change expression between the large oncosomes and exosomes. The positive numbers indicate genes that are expressed in large oncosomes but not in exosomes.

| Gene | LO/Exo |
| --- | --- |
| HBA1 | 3.5 |
| MTRNR2L2 | −3.2 |
| MT1G | −3.2 |
| MTRNR2L9 | −3.1 |
| HIST3H3 | 2.9 |
| DERL3 | 2.7 |
| DAPL1 | −2.7 |
| HBB | 2.6 |
| HSPA5 | −2.5 |
| POTEM | 2.5 |
| SCHIP1 | 2.4 |
| HBA2 | 2.4 |
| PLAC9 | −2.3 |
| FCER1G | 2.3 |
| HYOU1 | −2.3 |
| APBB3 | −2.3 |
| HSF4 | −2.2 |
| BEX4 | −2.2 |
| SLC7A5 | −2.2 |
| MTRNR2L8 | −2.1 |

TABLE 6

The genes with the highest fold-change expression between the large oncosomes and U87 cells. The positive values indicate markers for glioblastoma.

| Gene | (LO/cells) |
| --- | --- |
| UBC | 9.5 |
| HIST1H3F | 7.1 |
| HIST1H3G | 7 |
| HIST1H2AJ | 6.5 |
| HIST1H2BM | 6.2 |
| HIST1H1B | 6.1 |
| UBE2C | 6.1 |
| TK1 | 6 |
| MYBL2 | 5.9 |
| HIST1H3B | 5.8 |
| HIST1H2AH | 5.7 |
| RRM2 | 5.6 |
| HIST1H3J | 5.5 |
| HIST1H2BI | 5.5 |
| HIST1H2BO | 5.4 |
| HIST1H2AI | 5.4 |
| ANLN | 5.4 |
| ARHGAP11A | 5.3 |
| RAB13 | 5.2 |
| ZWINT | 5.1 |

TABLE 7

The genes with the highest fold-change mean expression between the normal and invasive lobular carcinoma (ILC) samples. The positive values indicate markers for ILC.

| Gene | Normal/ILC |
| --- | --- |
| KRTAP6-1 | 5.1 |
| HBG1 | 4.8 |
| TNP1 | −4.5 |
| AHSP | 4.5 |
| SPC24 | 4.5 |
| HBE1 | 4.3 |
| KCNH2 | 4.3 |
| SLC43A1 | 4.3 |
| MT1M | −4.2 |
| CENPF | 4.2 |
| G0S2 | −4.2 |
| KRTAP13-3 | 4.1 |
| ENO3 | −4 |
| MT1A | 4 |
| FHDC1 | 4 |
| SMR3A | 3.9 |
| SPTA1 | 3.9 |
| CA1 | 3.8 |
| PRM1 | −3.8 |
| TSPO2 | 3.8 |

TABLE 8

The genes with the highest fold-change mean expression between the normal and breast cancer samples. The positive values indicate markers for breast cancer.

| Gene | Normal/ILC |
| --- | --- |
| NXF3 | 5.2 |
| LOC650293 | 4.6 |
| TNP1 | −4.5 |
| G0S2 | −4.3 |
| MT1M | −4.2 |
| PAM16 | 4.2 |
| PRB2 | 4.1 |
| ANP32C | 4 |
| ACTG2 | −3.9 |
| FOS | −3.8 |
| ENO3 | −3.8 |
| KRTAP10-12 | 3.7 |
| KRTAP19-1 | −3.7 |
| APOBEC3H | 3.7 |
| SPC24 | 3.7 |
| PRB4 | 3.7 |
| LHB | 3.7 |
| S100A3 | 3.7 |
| SSX7 | 3.6 |
| MYL2 | −3.6 |

This is the first study on global mRNA characterization of two types of EVs (LO and Exo) with in-depth comparison to the donor cell using RNA-Seq. It is also the first attempt to use expression data to determine what factors influence the abundance of different mRNAs in the EVs. Finally, this is the first whole transcriptome analysis of EVs circulating in the plasma of patients with breast cancer. Our results demonstrate that 1) the transcripts exported in EVs are mostly of cytosolic origin, 2) the EV transcriptome is enriched in S-phase specific transcripts and exhibits a distinct signature (high E2F targets and histones, and low signal peptide) that discriminates them from the donor cell, 3) LO and Exo exhibit an overall similar mRNA cargo, however they show differences that might be functionally relevant, and 4) the EV signature can be detected in plasma of patients with breast cancer versus controls, along with transcripts that are upregulated in breast cancer tissues.

Our demonstration that most of the mRNAs exported in two different types of EVs derive from the cytosol, and that this might occur during the S-phase of the cell cycle, is in agreement with previous studies hypothesizing that EV shedding might be cell cycle-depend ent. The findings also highlight a common, perhaps universal feature of EV mRNA biology. In fact an mRNA pattern, similar to that we identified by RNA-Seq in our EV preparations, was found in array data from published studies on EVs across distinct systems, including breast cancer models. The appearance of this same pattern in plasma of patients with breast cancer suggests that identification of this EV signature in vivo might be indicative of increased EV shedding in patients with cancer. This promising result could be followed up by studies aimed to test whether a panel of known E2F targets and histones, combined with signal peptide genes, could be used to screen circulating EVs in patients with cancer. The identification of breast cancer specific transcripts suggests that analysis of EV RNA could result in potentially useful biomarkers. If validated on larger cohorts, this result could help ongoing efforts to improve the current tools for early diagnosis of breast cancer using minimally invasive methods.

Our results also have important implications for future attempts to study EV mRNA cargo. As we show here, the EV content is likely derived from cytosol, rather than whole cells. While EV mRNA has typically been compared to whole-cell mRNA from the donor source, our results suggest that comparisons between EVs and cytosolic mRNA are more appropriate to refine which mRNAs are enriched or excluded from the EVs during their formation. Importantly, this is one of the first studies of this kind, and the depth of the sequencing in our samples, both in vitro and in the circulation, was very high, allowing us to identify a larger number of genes than a previous study, in which the abundance of ribosomal and/or other RNA types precluded in-depth comparison of mRNAs expression between the Exo and the source cells.

Recent studies have described surprising heterogeneity in EV populations and have provided evidence that EVs originating from distinct intracellular origins (but from the same cell donor) might contain diverse cargo and play specialized functions. In line with this, our group has demonstrated that 25% of the protein cargo of LO and Exo purified from the same cell source is significantly different. However, this study shows a much more similar RNA profile among the two EV populations, with only 5% of the transcripts present at a difference greater than 2 fold in LO versus Exo. In vivo, the EV signature was identified by whole transcriptome analysis of a mixture of EVs from patients. Whether one population of EVs contributes to this signature more than another remains unresolved. Ultimately, this study highlights the possibility that a combinatorial analysis of different EV subsets might be a more relevant source for liquid biopsy than either particle alone. Future studies to clarify whether the tumour signal can be increased by improved purification methods are warranted.

With respect to the differences between LO and Exo (5% of the transcripts are at least 2-fold different between the sets), we observed an interesting functional trend. Most of the transcripts that were enriched in LO versus Exo encode proteins involved in important plasma membrane functions, and some of them for proteins with key functional roles in tumor progression and previously considered Exo resident molecules (e.g., VEGFA). An extracellular function for VEGFA, which is enriched in glioblastoma-derived EVs and capable to induce angiogenesis in recipient endothelial cells, has been previously demonstrated. Our demonstration that VEGFA mRNA levels are increased in endothelial cells exposed to LO is interesting and provocative. It might be in agreement with published reports that suggest that EVs can transfer RNA to target cells.

However, our observation that VEGFA mRNA levels increase as a response to LO treatment for 24 hours, but not for 6 hours, argues against RNA transfer in this case, and rather suggests that LO might be inducing mRNA expression in target cells. Additional studies using tagged constructs will be necessary for a more definitive conclusion. Indeed, functionally relevant is also the observed enrichment of HSPA5 mRNA in LO. We had previously identified the protein as a potential LO marker by mass spectrometry, and here we show that it is also enriched at the mRNA level in a different type of cell line[11].

In summary, this study represents the most extensive use of NGS profiling of EV mRNA, including two distinct classes of tumor-derived EVs. Our study has shown that EVs carry tumor-specific alterations and can be interrogated as a source of cancer-derived cargo. Because sample size and the number of RNA sequencing reads directly influence the accuracy of molecular subtyping, continuing improvements in technology will allow the translation of these findings to the clinic. Our methods did not distinguish between RNA present as full-length transcripts versus fragmented RNA. Hence, understanding whether intact transcripts can be shed in EVs is also an important question for exploration in future studies.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

The invention claimed is:

1. A method for determining the likelihood of cancer and treating the cancer in a subject in need thereof comprising:

obtaining results of levels of mRNA encoded by histone genes and E2F-target genes in extracellular vesicles isolated from a sample obtained from the subject, wherein the histones are HIST1H3F, HIST1H3G, HIST1H2AJ, HIST1H2BM, HIST1H1B, HIST1H3B, HIST1H2AH, HIST1H3J, HIST1H2BI, HIST1H2BO and HIST1H2AI, and the E2F targets are SPC24, CENPF, ARHGAP11B, CEP128, QPCTL, HM MR, HIST1H2BL, NDC80, KIF15, HMBS, ABCB6, HIST1H2BM, GUCY1B3, SYNGR4, RECQL4, CDCA7, TTK, CKAP2, BORA and CENPW; and determining that the subject has an increased likelihood of having cancer when the sample from the subject comprises increased levels of the mRNAs encoded by the histone and E2F target genes relative to a reference value; and administering an effective amount of a therapy selected from the group consisting of surgery, radiation, chemotherapy, immunotherapy, vaccine, and combinations thereof to treat the cancer to the subject having the increased likelihood of having cancer.

2. The method of claim 1, wherein the extracellular vesicles are microvesicles, exosomes, large oncosomes or a combination thereof.

3. The method of claim 1, wherein the sample is blood, plasma or combination thereof.

4. The method of claim 1 wherein the subject is human.

5. The method of claim 1, wherein the reference value is the mean or median levels of the mRNA in a population of subjects that do not have cancer.

6. The method of claim 1, wherein the reference value is the mean or median levels of the mRNA in a population of subjects that have cancer in remission.

7. The method of claim 1, wherein the reference value is the mean or median levels of the mRNA obtained from the subject at a difference time point.

* * * * *